(12) United States Patent
English

(10) Patent No.: US 11,866,691 B2
(45) Date of Patent: Jan. 9, 2024

(54) METHOD FOR CREATING A STIFF, RIGID MYCELIUM-BASED BIOCOMPOSITE MATERIAL FOR USE IN STRUCTURAL AND NON-STRUCTURAL APPLICATIONS

(71) Applicant: Joshua Aaron English, San Diego, CA (US)

(72) Inventor: Joshua English, San Diego, CA (US)

(73) Assignee: okom wrks labs, PBC, Solana Beach, CA (US)

( * ) Notice: Subject to any disclaimer, the term of this patent is extended or adjusted under 35 U.S.C. 154(b) by 31 days.

(21) Appl. No.: 17/344,882

(22) Filed: Jun. 10, 2021

(65) Prior Publication Data

US 2022/0098545 A1 Mar. 31, 2022

Related U.S. Application Data

(60) Provisional application No. 62/705,100, filed on Jun. 10, 2020.

(51) Int. Cl.
*C12N 1/14* (2006.01)
*B33Y 80/00* (2015.01)
*B33Y 70/00* (2020.01)
*B33Y 10/00* (2015.01)

(52) U.S. Cl.
CPC ............... *C12N 1/14* (2013.01); *B33Y 70/00* (2014.12); *B33Y 80/00* (2014.12); *B33Y 10/00* (2014.12); *C12N 2513/00* (2013.01); *C12N 2533/90* (2013.01)

(58) Field of Classification Search
CPC ...... C12N 1/14; C12N 2533/90; B33Y 10/00; B33Y 70/00; B33Y 80/00
See application file for complete search history.

(56) References Cited

U.S. PATENT DOCUMENTS

| | | | |
|---|---|---|---|
| 5,854,056 A | 12/1998 | Dschida | |
| 8,001,719 B2 | 8/2011 | Bayer et al. | |
| 8,227,224 B2 | 7/2012 | Kalisz et al. | |
| 8,227,225 B2 | 7/2012 | Rocco et al. | |
| 8,227,233 B2 | 7/2012 | Kalisz et al. | |
| 8,283,153 B2 | 10/2012 | Rocco et al. | |
| 8,298,809 B2 | 10/2012 | Kalisz et al. | |
| 8,298,810 B2 | 10/2012 | Rocco et al. | |
| 8,313,939 B2 | 11/2012 | Kalisz et al. | |
| 8,999,687 B2 | 4/2015 | Bayer et al. | |
| 9,085,763 B2 | 7/2015 | Winiski et al. | |
| 9,253,889 B2 | 2/2016 | Bayer et al. | |
| 9,394,512 B2 | 7/2016 | Bayer et al. | |
| 9,410,116 B2 | 8/2016 | Ross | |
| 9,469,838 B2 | 10/2016 | Schaak et al. | |
| 9,485,917 B2 | 11/2016 | Bayer et al. | |
| 9,555,395 B2 | 1/2017 | Araldi et al. | |
| 9,714,180 B2 | 7/2017 | McIntyre et al. | |
| 9,803,171 B2 | 10/2017 | Bayer et al. | |
| 9,879,219 B2 | 1/2018 | McIntyre et al. | |
| 9,914,906 B2 | 3/2018 | Winiski et al. | |
| 10,125,347 B2 | 11/2018 | Winiski | |
| 10,144,149 B2 | 12/2018 | McIntyre et al. | |
| 10,154,627 B2 | 12/2018 | Mcintyre et al. | |
| 10,266,695 B2 | 4/2019 | Lucht et al. | |
| 10,537,070 B2 | 1/2020 | Betts et al. | |
| 10,583,626 B2 | 3/2020 | Bayer et al. | |
| 10,589,489 B2 | 3/2020 | Bayer et al. | |
| 10,999,687 B2 | 5/2021 | Lee et al. | |
| 11,015,059 B2 | 5/2021 | Smith et al. | |
| 2008/0264858 A1 | 10/2008 | Stamets | |
| 2011/0266831 A1 | 11/2011 | Kalisz et al. | |
| 2011/0306107 A1 | 12/2011 | Kalisz et al. | |
| 2012/0124839 A1 | 5/2012 | Kalisz et al. | |
| 2012/0135504 A1 | 5/2012 | Ross | |
| 2012/0225471 A1 | 9/2012 | McIntyre et al. | |
| 2012/0270302 A1 | 10/2012 | Bayer et al. | |
| 2012/0315687 A1 | 12/2012 | Bayer et al. | |
| 2013/0095560 A1 | 4/2013 | McIntyre et al. | |
| 2013/0202855 A1 | 8/2013 | Kalisz et al. | |
| 2013/0263500 A1 | 10/2013 | McIntyre et al. | |
| 2013/0309755 A1 | 11/2013 | McIntyre et al. | |
| 2014/0056653 A1 | 2/2014 | Scully et al. | |

(Continued)

FOREIGN PATENT DOCUMENTS

| | | |
|---|---|---|
| AU | 2013-251269 A1 | 11/2013 |
| AU | 2015-271910 A1 | 7/2017 |

(Continued)

OTHER PUBLICATIONS

Jones et al. "Engineered mycelium composite construction materials from fungal biorefineries: A critical review", Materials and Design,vol. 187, Feb. 2020, 108397 (Year: 2020).*

Heisel et al., "Design, Cultivation and Application of Load-Bearing Mycelium Components: The MycoTree at the 2017 Seoul Biennale of Architecture and Urbanism", International Journal of Sustainable Energy Development (IJSED), vol. 6, Issue 1, Jun. 2017/18 (Year: 2018).*

Da Conceição van Nieuwenhuizen et al., "The compressive strength of mycelium derived from a mushroom production process", Academic Journal of Civil Engineering, 35(2), 265-271, 2017 (Year: 2017).*

(Continued)

*Primary Examiner* — Ruth A Davis
(74) *Attorney, Agent, or Firm* — Faegre Drinker Biddle & Reath LLP

(57) ABSTRACT

The present invention provides an improved method of utilizing agricultural waste and fungal mycelium in order to create mycelium-based biocomposite materials capable of serving in structural, load-bearing capacities. The dramatic reduction in the embodied carbon of a part grown with the method of the present invention over prior art creates benefit for the use of mycelium-based biocomposites in a new, regenerative economy. The present invention creates parts of superior strength over prior art using far less embodied carbon in the process of manufacture.

19 Claims, 11 Drawing Sheets

(56) References Cited

U.S. PATENT DOCUMENTS

| | | |
|---|---|---|
| 2014/0069004 A1 | 3/2014 | Bayer et al. |
| 2014/0186927 A1 | 7/2014 | Winiski et al. |
| 2015/0033620 A1 | 2/2015 | Greetham et al. |
| 2015/0101509 A1 | 4/2015 | McIntyre et al. |
| 2015/0247115 A1 | 9/2015 | Bayer et al. |
| 2015/0342138 A1 | 12/2015 | Bayer et al. |
| 2016/0302364 A1 | 10/2016 | Lucht et al. |
| 2016/0302365 A1 | 10/2016 | Betts et al. |
| 2016/0355779 A1 | 12/2016 | Ross |
| 2017/0028600 A1 | 2/2017 | McIntyre et al. |
| 2017/0253852 A1 | 9/2017 | Bayer et al. |
| 2018/0014468 A1 | 1/2018 | Ross et al. |
| 2018/0146627 A1 | 5/2018 | Ross et al. |
| 2018/0148682 A1 | 5/2018 | Ross |
| 2018/0282529 A1 | 10/2018 | Kaplan-Bie |
| 2019/0090436 A1 | 3/2019 | Betts et al. |
| 2019/0284307 A1 | 9/2019 | Chase et al. |
| 2019/0338240 A1 | 11/2019 | Carlton et al. |
| 2019/0357454 A1 | 11/2019 | Mueller et al. |
| 2019/0359931 A1 | 11/2019 | Mueller et al. |
| 2019/0390156 A1 | 12/2019 | Bayer et al. |
| 2019/0390399 A1 | 12/2019 | Chase et al. |
| 2020/0024577 A1 | 1/2020 | Carlton et al. |
| 2020/0025672 A1 | 1/2020 | Scullin et al. |
| 2020/0055274 A1 | 2/2020 | Bayer et al. |
| 2020/0102530 A1 | 4/2020 | Winiski, I et al. |
| 2020/0120880 A1 | 4/2020 | Ross et al. |
| 2020/0128763 A1 | 4/2020 | Ross |
| 2020/0131694 A1 | 4/2020 | Scullin et al. |
| 2020/0157506 A1 | 5/2020 | Bayer et al. |
| 2020/0196541 A1 | 6/2020 | Ross et al. |
| 2020/0239830 A1 | 7/2020 | O'Brien et al. |
| 2021/0037721 A1 | 2/2021 | Ross et al. |
| 2021/0127601 A9 | 5/2021 | Kaplan-Bie et al. |
| 2021/0198621 A1 | 7/2021 | Ross |
| 2021/0267142 A1 | 9/2021 | Ross et al. |
| 2021/0298249 A1 | 9/2021 | Ross et al. |
| 2021/0329853 A1 | 10/2021 | Ross et al. |
| 2021/0348117 A9 | 11/2021 | Winiski |

FOREIGN PATENT DOCUMENTS

| | | |
|---|---|---|
| AU | 2015-271912 A1 | 7/2017 |
| CA | 2915179 A1 | 6/2017 |
| CA | 2915182 A1 | 6/2017 |
| CA | 3100861 A1 | 1/2020 |
| SI | 2094856 T1 | 7/2016 |
| WO | 2010/005476 A1 | 1/2010 |
| WO | WO-2012-122092 A2 | 9/2012 |
| WO | WO-2014-031810 A2 | 2/2014 |
| WO | WO-2015-050620 A1 | 4/2015 |
| WO | WO-2016-149002 A1 | 9/2016 |
| WO | 2018/014004 A1 | 1/2018 |
| WO | WO-2018-183735 A1 | 10/2018 |
| WO | WO-2019-099474 A1 | 5/2019 |
| WO | WO-2019-178406 A1 | 9/2019 |
| WO | WO-2019-226823 A1 | 11/2019 |
| WO | WO-2020-082043 A1 | 4/2020 |
| WO | WO-2020-082044 A1 | 4/2020 |
| WO | WO-2020-086907 A1 | 4/2020 |
| WO | WO-2020-087033 A1 | 4/2020 |
| WO | WO-2020-154722 A1 | 7/2020 |
| WO | WO-2020-186068 A1 | 9/2020 |
| WO | WO-2021-092051 A1 | 5/2021 |
| WO | WO-2021-158678 A1 | 8/2021 |

OTHER PUBLICATIONS

Cowley et al., "Cellular Debris, Not Mucilage Polysaccharides, Dominate Extracts of Plantago Ovata and Plantago Lanceolata Calli Grown in Vitro," bioExiv The preprint server for biology, Jun. 21, 2020, Retrievedd from https://www.biorxiv.org/content/10.1101/2020.06.15.153395v2.

Critical Concrete "Building with Mushrooms" Apr. 23, 2018, Retrieved from https://criticalconcrete.com/building-with-mushrooms/.

Crowther et al., "Functional and Ecological Consequences of Saprotrophic Fungus-Grazer Interactions," The ISME Journal, vol. 6, No. 11, Nov. 2012, pp. 1992-2001.

Dente et al., "Carbon-Storing, Straw Structurally Insulated Panels and Their Potential Impact on the Domestic Building Industry," Retrieved from https://youtu.be/O6NTR-RMt3s. U.S. EPA Webina, Online.

Dessi-Olive, J., "Craft and Structural Innovation of Mycelium Structures in Architectural Education," CRC Press, Structures and Architecture A Viable Urban Perspective?, 1st edition, 2022, pp. 43-50.

Dessi-Olive, J., "Strategies for Growing Large-Scale Mycelium Structures," Biomimetics, vol. 7, No. 3, Sep. 2022, pp. 129.

Donnarumma et al., "Focus on Apparel Complexity: Cotton Fabric Topography by CLSM," Materials Today, Jun. 2, 2021, Retrieved from https://www.materialstoday.com/characterization/comment/focus-on- apparel-complexity/.

Elfordy t al., "Mechanical and Thermal Properties of Lime and Hemp Concrete ('Hempcrete') Manufactured by a Projection Process," Construction and Building Materials, vol. 22, No. 10, Oct. 2008, pp. 2116-2123.

Elsacker et al., "A Comprehensive Framework for the Production of Mycelium-Based Lignocellulosic Composites," Science of The Total Environment, vol. 725, Jul. 2020, pp. 138431.

Elsacker et al., "Mechanical, Physical and Chemical Characterisation of Mycelium-Based Composites with Different Types of Lignocellulosic Substrates," PLOS One, vol. 14, Jul. 2019, pp. e0213954.

Elsacker et al., "Mycelium-Based Materials at the Dawn of the Anthropocene," 2019, pp. 1083-1090.

Elsacker, E. V., " Mycelium Matters—An Interdisciplinary Exploration of the Fabrication and Properties of Mycelium-Based Materials," Apr. 20, 2021, 469 pages.

Emrath, P., "Higher Lumber Costs Add More Than $35K to New Home Prices, $119 to Monthly Rent," I Eye On Housing, Apr. 28, 2021, Retrieved from https://eyeonhousing.org/2021/04/higher-lumber-costs-add-more-than-35k-to-new-home-prices-119-to-monthly-rent/?_ga=2.198182188.2008231385.1619999096-64896830.1619999096.

Endrei et al., "3D Printed Formwork for Concrete: State-of-the-Art, Opportunities, Challenges, and Applications," 3D Printing and Additive Manufacturing, vol. 9, No. 2, Apr. 11, 2022, pp. 85-107.

Engle, J., "How Much Money Is an Acre of Timber Worth?," Dec. 16, 2021, Retrieved from https://www.forest2market.com/blog/how-much-money-is-an-acre-of-timber-worth.

Fairus et al., "Mycelium-Based Composite: A Way Forward for Renewable Material," Journal of Sustainability Science and Management, vol. 17, No. 1, Jan. 2022, pp. 271-280.

Fang et al., "Role of Fungal-Mediated Mineralization in Biocementation of Sand and Its Improved Compressive Strength," International Biodeterioration & Biodegradation, vol. 133, Sep. 2018, pp. 216-220.

Fathomers, "Phil Ross," Apr. 10, 2020, URL—https://fathomers.org/phil-ross.

Feickert et al., "Thin Shell Foundations: Embodied Carbon Reduction through Materially Efficient Geometry," MIT Libraries , May 2022, Retrieved from https://dspace.mit.edu/handle/1721.1/144920.

Feldman, D., "Fungi—the Sustainable Alternative to Plastic & Wood," The Permaculture Research Institute, Dec. 31, 2015, Retrieved from https://www.permaculturenews.org/2015/12/31/fungi-the-sustainable-alternative-to-plastic-wood/.

Fifty Years, "MycoWorks Mycelium Leather—Philip Ross at Impact. Tech at Google SF HQ," YouTube, 2016, URL—https://www.youtube.com/watch?v=PBxzYCj662s.

Fleming, M., "Climate Crisis Is Here. There Is Only One Solution," We The Peoples, Aug. 3, 2021, Retrieved from https://medium.com/we-the-peoples/climate crisis-is-here-there-is-only-one-solution-1a82c3682068.

Food and Agriculture Organization of the United Nations. State of the World's Forests 2020: Forestry, Biodiversity and People. Food & Agriculture Org, 2020.

(56) References Cited

OTHER PUBLICATIONS

Forrester, J. W., "Counterintuitive Behavior of Social Systems," Theory and Decision, vol. 2, No. 2, Dec. 1971, pp. 109-140.
Forrester, J. W., "System Dynamics and the Lessons of 35 Years," A Systems-Based Approach to Policymaking, 1993, pp. 199-240.
Fullerton, J., "Regenerative Capitalism," pp. 120.
Gamalero et al., "Beneficial Role of Plant Growth Promoting Bacteria and Arbuscular Mycorrhizal Fungi on Plant Responses to Heavy Metal Stress," Canadian Journal of Microbiology, vol. 55, No. 5, May 2009, pp. 501-514.
Ganal, El-Awad El-Daw, "A Study of Guar Seed Amd Guar Gum Properties,". University of Khartoum, Jun. 1998, Retrievedd from https://www.osti.gov/etdeweb/servlets/purl/20082078.
Gao et al., "Recent Advances in Microfluidic-Aided Chitosan-Based Multifunctional Materials for Biomedical Applications," International Journal of Pharmaceutics, vol. 600, May 2021, pp. 120465.
Ghafoor et al., "Comparative Study of the Life Cycle Embodied Greenhouse Gas Emissions of Panelised Prefabricated Residential Walling Systems in Australia," 54th International Conference of the Architectural Science Association, 2020, pp. 256-265, Retrievedd from https://minerva-access.unimelb.edu.au/items/bf42098f-3123-5bb1-ab7e-369d9e0c227c.
Ghazvinian et al., "Mycelium-Based Bio-Composites For Architecture: Assessing the Effects of Cultivation Factors on Compressive Strength," 2019, Retrievedd from https://doi.org/10.5151/proceedings- ecaadesigradi2019_465.
Girometta et al., "Physico-Mechanical and Thermodynamic Properties of Mycelium-Based Biocomposites: A Review," Sustainability, vol. 11, No. 1, Jan. 2019, pp. 281.
Gonçalves et al., "Thermal Insulators Made with Rice Husk Ashes: Production and Correlation between Properties and Microstructure," Construction and Building Materials, vol. 21, No. 12, Dec. 2007, pp. 2059-2065.
Gorchs et al., "Effect of Hemp (Cannabis sativa L.) in a Crop Rotation Hemp-Wheat in the Humid Cool Areas of North-Eastern of Spain," Proceeding of the Conference: Crop Development for the Cool and Wet Regions of Europe (COST Action 814), 2000, pp. 581-589.
Grover, A., "The Future Is Fungal: Interview with Phil Ross," Glasstire, Sep. 8, 2012, URL—https://glasstire.com/2012/09/08/the-future-is-fungal-interview-with-phil-ross/.
Grushkin, D.,"The Next Leather Jacket Will Be Made From Mushrooms," Popular Science, Aug. 10, 2016 Retrievedd from https://www.popsci.com/next-leather-jacket-will-made-from-mushrooms/.
Haldar et al., "A Critical Review on the Effect of Lignin Redeposition on Biomass in Controlling the Process of Enzymatic Hydrolysis," BioEnergy Research, vol. 15, No. 2, Jun. 2022, pp. 863-874.
Hamilton et al., "2020 Global Status Report for Buildings and Construction: Towards a Zero-Emissions, Efficient and Resilient Buildings and Construction Sector," United Nations environment programme, Dec. 16, 2020, pp. 79, URL—https://globalabc.org/sites/default/files/inline-files/2020%20Buildings%20GSR_FULL%20REPORT.pdf.
Haneef et al., "Advanced Materials From Fungal Mycelium: Fabrication and Tuning of Physical Properties," Scientific Reports, vol. 7, No. 1, Jan. 24, 2017, pp. 41292.
Hasanin et al., "Green Enhancement of Wood Plastic Composite Based on Agriculture Wastes Compatibility via Fungal Enzymes," Scientific Reports, vol. 12, No. 1, Nov. 2022, pp. 19197.
Hebel et al., "Process-Controlled Optimization of the Tensile Strength of Bamboo Fiber Composites for Structural Applications," Composites Part B: Engineering, vol. 67, Dec. 2014, pp. 125-131.
Held et al., "Intracellular Mechanisms of Fungal Space Searching in Microenvironments," Proceedings of the National Academy of Sciences of the United States of America, vol. 116, No. 27, Jul. 2019, pp. 13543-13552.
Held et al., "Microfluidics Structures for Probing the Dynamic Behaviour of Filamentous Fungi," The 35th International Conference on Micro- and Nano-Engineering (MNE), vol. 87, No. 5, May 2010, pp. 786-789.
Herman et al., "Growth Induced Translocation Effectively Directs an Amino Acid Analogue to Developing Zones in Agaricus Bisporus," Fungal Biology, vol. 124, No. 12, Dec. 2020, pp. 1013-1023.
Hoeppner et al., "Proteins and Their Ligands: Their Importance and How to Crystallize Them," Advanced Topics on Crystal Growth, Feb. 20, 2013.
Holt et al., "Fungal Mycelium and Cotton Plant Materials in the Manufacture of Biodegradable Molded Packaging Material: Evaluation Study of Select Blends of Cotton Byproducts," Journal of Biobased Materials and Bioenergy, vol. 6, No. 4, Aug. 2012, pp. 431-439.
Howell et al., "Temporal Changes in Wood Crystalline Cellulose during Degradation by Brown Rot Fungi," International Biodeterioration & Biodegradation, vol. 63, No. 4, Jun. 2009, pp. 414-419.
Hsieh et al., "Nitrogen Removal from Urban Stormwater Runoff Through Layered Bioretention Columns," Water Environment Research, vol. 79, No. 12, Nov. 2007, pp. 2404-2411.
Hu et al., "Effect of a Novel Chitosan-Based Flame Retardant on Thermal and Flammability Properties of Polyvinyl Alcohol," Journal of Thermal Analysis and Calorimetry, vol. 112, No. 2, May 2013, pp. 859-864.
Interviews with MycoWorks Co-Founders Phil Ross & Sophia Wang. Directed by Ross Philip, 2016. YouTube, https://www.youtube.com/watch?v=LFoiXFbvSBQ.
More et al., "A Review of Lignin Hydrogen Peroxide Oxidation Chemistry with Emphasis on Aromatic Aldehydes and Acids," Holzforschung, vol. 75, No. 9, Sep. 2021, pp. 806-823.
Motherboard, "Fungus: The Plastic of the Future," 2015. YouTube, Retrievedd from https://www.youtube.com/watch?v=jnMXH5TqqG8.
Mucha carne "Mycelium Bricks," YouTube, Directed by Ross Philip, 2016, URL—https://www.youtube.com/watch?v=IHhVpXCpTA0.
Mwaikambo et al., "Chemical Modification of Hemp, Sisal, Jute, and Kapok Fibers by Alkalization," Journal of Applied Polymer Science, vol. 84, No. 12, Jun. 2002, pp. 2222-2234.
Mwaikambo et al., "The Effect of Chemical Treatment on the Properties of Hemp, Sisal, Jute and Kapok for Composite Reinforcement," Die Angewandte Makromolekulare Chemie, vol. 272, No. 1, Dec. 1999, pp. 108-116.
MycoWorks, "How to Make a Myco-Brick," YouTube, Directed by Ross Philip, 2016, URL—https://www.youtube.com/watch?v=c6nurN-Hii8.
Nadezda et al., "Properties Characterization of Chemically Modified Hemp Hurds," Materials, vol. 7, No. 12, Dec. 2014, pp. 8131-8150.
Nakamura et al., "Studies on Bound Water of Cellulose by Differential Scanning Calorimetry," Textile Research Journal, vol. 51, No. 9, Sep. 1981, pp. 607-613.
Nguyen et al., "Mycomerge: Fabrication of Mycelium-Based Natural Fiber Reinforced Composites on a Rattan Framework," Biomimetics, vol. 7, No. 2, Apr. 2022, pp. 42(1-13).
NRDC, "Our Forests Aren't Fuel,"Jul. 29, 2021, Retrieved from https://www.nrdc.org/resources/our-forests- arent-fuel.
NRDC, "PAndora's Box: Clearcutting in the Canadian Boreal Unleashes Millions of Tons of Previously Uncounted Carbon Dioxide Emissions," Mar. 2018, URL—https://www.nrdc.org/sites/default/files/pandoras-box-clearcutting-boreal-carbon-dioxide-emissions-ip.pdf.
Nutsubidze et al., "Consecutive Polymerization and Depolymerization of Kraft Lignin by Trametes Cingulata fn1" Phytochemistry, vol. 49, No. 5, Nov. 5, 1998, pp. 1203-1212.
Oliver et al., "Carbon, Fossil Fuel, and Biodiversity Mitigation With Wood and Forests," Journal of Sustainable Forestry, vol. 33, No. 3, Apr. 2014, pp. 248-275.
Ongpeng et al., "Using Waste in Producing Bio-Composite Mycelium Bricks," Applied Sciences, vol. 10, No. 15, Jul. 2020, pp. 5303.
Oregon Wild "Forest-Carbon 101," Nov. 18, 2022, Retrievedd from http://www.oregonwild.org/forests/climate-change/forest-carbon-101.
Orina et al., "Use of High-Resolution X-Ray Micro-Computed Tomography for the Analysis of Internal Structural Changes in Maize Infected with Fusarium Verticillioides," Food Analytical Methods, vol. 10, No. 9, Sep. 2017, pp. 2919-2933.

(56) References Cited

OTHER PUBLICATIONS

Ouajai et al., "Composition, Structure and Thermal Degradation of Hemp Cellulose after Chemical Treatments," Polymer Degradation and Stability, vol. 89, No. 2, Aug. 2005, pp. 327-335.
Ozkan, D. "Mycelium Sausages," My Site, Jul. 30, 2021, Retrievedd from https://www.mycologyforarchitecture.com/post/mycelium-sausages.
Pallua et al., "Application of Micro-Computed Tomography to Microstructure Studies of the Medicinal Fungus Hericium Coralloides," Mycologia, vol. 107, No. 1, Jan. 2015, pp. 227-238.
Pejic et al., "The Effects of Hemicelluloses and Lignin Removal on Water Uptake Behavior of Hemp Fibers," Bioresource Technology, vol. 99, No. 15, Oct. 2008, pp. 7152-7159.
Pelletier et al., "An Evaluation Study of Mycelium Based Acoustic Absorbers Grown on Agricultural By-Product Substrates," Industrial Crops and Products, vol. 51, Nov. 2013, pp. 480-485.
Penn State Extension "Forest Finance 8: To Cut or Not Cut-Deciding When to Harvest Timber," Nov. 18, 2021, Retrieved from https://extension.psu.edu/forest-finance-8-to-cut-or-not-cut-deciding-when-to-harvest-timber.
Peters, A., "This Beautiful Carbon-Neutral 'Leather' Is Grown From Mushrooms," Fast Company, Jul. 29, 2016, URL—https://www.fastcompany.com/3062236/this-beautiful-carbon-neutral-leather-is-grown-from- mushrooms.
Philip Ross Inventions, "Patents and Patent Applications—Justia Patents Search," Apr. 10, 2020, URL—https://patents.justia.com/inventor/philip-ross?page=2.
Pinage et al., "Long-Term Impacts of Selective Logging on Amazon Forest Dynamics from Multi-Temporal Airborne LiDAR," Remote Sensing, vol. 11, No. 6, 2019, pp. 709 (1-21).
Piponiot et al., "Optimal Strategies of Ecosystem Services Provision for Amazonian Production Forests," Environmental Research Letters, Dec. 2019, URL—https://doi.org/10.1088/1748-9326/ab5eb1.
Potapov et al., "Intact Forest Landscapes," Intact Forest Landscapes, Dec. 10, 2021, URL—http://www.intactforests.org/index.html.
Putz et al., "Improved Tropical Forest Management for Carbon Retention," Plos Biology, vol. 6, No. 7, Jul. 2008, pp. 1368-1369.
Rafiee et al., "Biodegradable Green Composites: It's Never Too Late to Mend," Current Opinion in Green and Sustainable Chemistry, vol. 30, Aug. 2021, pp. 100482.
Rammer et al., "Performance of Structural Insulated Panel Walls under Seismic Loading," Joint Research, United States Department of Agriculture, Sep. 2020, pp. 62.
Rappa et al., "R&D Life Cycles," Mar. 28, 2021, URL—https://www.cga.ct.gov/2015/rpt/2015-R-0207.htm.
Raut et al., "Fungal Based Biopolymer Composites for Construction Materials," Materials, vol. 14, No. 11, May 2021, pp. 2906 (1-20).
Research Features "Mycology: Unravelling the Riddle of the Filamentous Fungi," Jun. 1, 2017, URL—https://researchfeatures.com/mycology-unravelling-riddle-filamentous-fungi-2/.
Riaz et al., "Arbuscular Mycorrhizal Fungi-Induced Mitigation of Heavy Metal Phytotoxicity in Metal Contaminated Soils: A Critical Review," Journal of Hazardous Materials, vol. 402, Jan. 2021, pp. 123919.
Riquelme et al., "Fungal Morphogenesis, from the Polarized Growth of Hyphae to Complex Reproduction and Infection Structures," Microbiology and Molecular Biology Reviews, vol. 82, No. 2, Apr. 2018, pp. e00068-17.
Riquelme et al., "The Spitzenkörper: A Choreographer of Fungal Growth and Morphogenesis," Host-Microbe Interactions: Fungi/Parasites/Viruses, vol. 20, Aug. 2014, pp. 27-33.
RMI "Carbon-Free Buildings," Retrievedd from https://rmi.org/our-work/buildings/. Accessed Feb. 9, 2023.
Rodrigues et al., "Boom-and-Bust Development Patterns Across the Amazon Deforestation Frontier," Science, vol. 324, No. 5933, Jun. 2009, pp. 1435-1437.
Roth-Johnson, L., "A House Made From Mushrooms? An Artist Dreams of a Fungal Future," KQED, Aug. 26, 2014. URL—https://www.kqed.org/quest/71171/a-house-made-from-mushrooms-an-artist-dreams-of-a- fungal-future.
Sàez et al., "Analyzing a Fungal Mycelium and Chipped Wood Composite for Use in Construction," 2021, URL—https://www.researchgate.net/publication/354321519_Analyzing_a_fungal_mycelium_and_chipped_wood_composite_for_use_in_construction.
Saez et al., "Developing Sandwich Panels with a Mid-Layer of Fungal Mycelium Composite for a Timber Panel Construction System," World Conference on Timber Engineering, 2021, 8 pages.
Saez et al., "Exploring the Binding Capacity of Mycelium and Wood-Based Composites for Use in Construction," Biomimetics, vol. 7, No. 2, Jun. 11, 2022, pp. 78 (1-8).
Santos et al., "Influence of Drying Heat Treatments on the Mechanical Behavior and Physico-Chemical Properties of Mycelial Biocomposite," Composites Part B: Engineering, vol. 217, Jul. 2021, pp. 108870.
Sassoni et al., "Novel Sustainable Hemp-Based Composites for Application in the Building Industry: Physical, Thermal and Mechanical Characterization," Energy and Buildings, vol. 77, Jul. 2014, pp. 219-226.
Savastano et al., "Fracture and Fatigue of Natural Fiber-Reinforced Cementitious Composites," Cement and Concrete Composites, vol. 31, No. 4, Apr. 2009, pp. 232-243.
Sawpan et al., "Effect of Various Chemical Treatments on the Fibre Structure and Tensile Properties of Industrial Hemp Fibres," Composites Part A: Applied Science and Manufacturing, vol. 42, No. 8, Aug. 2011, pp. 888-895.
SciFri, "The Fungi in Your Future," 2016. YouTube, URL—https://www.youtube.com/watch?v=jBXGFOk5_Rs.
Scott, A., "Philip Ross Crafts Furniture from Mycelium—SFGate," Dec. 16, 2012, URL—https://www.sfgate.com/homeandgarden/article/Philip-Ross-crafts-furniture-from-mycelium-4116989.php.
Segal et al., "An Empirical Method for Estimating the Degree of Crystallinity of Native Cellulose Using the X-Ray Diffractometer," Textile Research Journal, vol. 29, No. 10, Oct. 1959, pp. 786-794.
Semuels, A., "Why Is the U.S. Still Using Wood to Build Houses?," Time, Jun. 16, 2021, URL—https://time.com/6046368/wood-steel-houses-fires/.
Soh et al., "Development of an Extrudable Paste to Build Mycelium-Bound Composites," Materials & Design, vol. 195, Oct. 2020, pp. 109058.
Space10. "Expert View: Biomaterials with Philip Ross," Medium, Apr. 5, 2018, URL—https://medium.com/space10-imagine/expert-view-biomaterials-with-philip-ross-7c28a09301a2.
Stanley et al., "Soil-on-a-Chip: Microfluidic Platforms for Environmental Organismal Studies," Lab Chip, vol. 16, No. 2, 2016, pp. 228-241.
Steinberg, G., "Endocytosis and Early Endosome Motility in Filamentous Fungi," Current Opinion in Microbiology, vol. 20, Aug. 2014, pp. 10-18.
Stephan et al., "A Comprehensive Assessment of the Life Cycle Energy Demand of Passive Houses," Applied Energy, vol. 112, Dec. 2013, pp. 23-34.
Stiebert et al., "Emission Omissions: Carbon Accounting Gaps in the Built Environment," IISD, Apr. 2019, pp. 1-74.
Suzanne Lee Lowry Inventions, "Patents and Patent Applications" Justia Patents Search, Apr. 10, 2020.
Suzanne Lee,"Suzanne Lee: Grow Your Own Clothes," 2011, YouTube, URL—https://www.youtube.com/watch?v=3p3-vI9VFYU.
Sydor et al., "Fungi in Mycelium-Based Composites: Usage and Recommendations," Materials, vol. 15, No. 18, Sep. 2022, pp. 6283 (1-34).
Sydor et al., "Mycelium-Based Composites in Art, Architecture, and Interior Design: A Review," Polymers, vol. 14, No. 1, Dec. 2021, pp. 145 (1-21).
Takeshita et al., "Interdependence of the Actin and the Microtubule Cytoskeleton during Fungal Growth," Current Opinion in Microbiology, vol. 20, 2014, pp. 34-41.

(56) References Cited

OTHER PUBLICATIONS

Talberth, J., "Oregon Forest Carbon Policy:Scientific and technical brief to guide legislative intervention," Version 1.0: Dec. 11, 2017, Center for Sustainable Economy, Dec. 2017, pp. 1-44, URL—https://www.streetroots.org/sites/default/files/Oregon%20Forest%20Carbon%20Policy%20Technical%20Brief%201.0.pdf.
Tech Brief, "Strategies for Improving the Sustainability of Concrete Pavements," Apr. 2016, pp. 1-28.
Tenenbaum, D. J., "Food vs. Fuel: Diversion of Crops Could Cause More Hunger," Environmental Health Perspectives, vol. 116, No. 6, Jun. 2008, pp. A254-A257.
Terpáková et al., "Chemical Modification of Hemp Shives and Their Characterization," Procedia Engineering, vol. 42, 2012, pp. 931-941.
The Construction Association, "Construction Material Costs Increase 7.4 Percent, as Contractors Continue to be Squeezed By Tariffs and Rising Fuel Prices," Oct. 10, 2018, Retrieved from https://www.agc.org/news/2018/10/10/construction-material-costs-increase-74-percent-contractors-continue-be squeezed.
The Guardian, "Photography Campaign Shows the Grim Aftermath of Logging in Canada's Fragile Forests," Dec. 2, 2020, URL—http://www.theguardian.com/world/2020/dec/02/canada-forests-clearcutting- ecosystem.
Thomas, N., "How Many Tons of Wood Are on an Acre of Land?," Dec. 16, 2021, URL—https://www.forest2market.com/blog/how-many-tons-of-wood-are-on-an-acre-of-land.
Thomsen et al., "Effects of Chemical-Physical Pre-Treatment Processes on Hemp Fibres for Reinforcement of Composites and for Textiles," Industrial Crops and Products, vol. 24, No. 2, Sep. 2006, pp. 113-118.
Thygesen et al., "Hemp Fiber Microstructure and Use of Fungal Defibration to Obtain Fibers for Composite Materials," Journal of Natural Fibers, vol. 2, No. 4, Mar. 2006, pp. 19-37.
Thygesen et al., "On the Determination of Crystallinity and Cellulose Content in Plant Fibres," Cellulose, vol. 12, No. 6, Dec. 2005, pp. 563-576.
Tripathi et al., "Biomass Waste Utilisation in Low-Carbon Products: Harnessing a Major Potential Resource," npj | Climate and Atmospheric Science, vol. 2, No. 1, Oct. 2019, pp. 35 (1-10).
Verdin et al., "Off the Wall: The Rhyme and Reason of Neurospora Crassa Hyphal Morphogenesis," The Cell Surface, vol. 5, Dec. 2019, p. 100020.
Vestin et al., "Impacts of Clear-Cutting of a Boreal Forest on Carbon Dioxide, Methane and Nitrous Oxide Fluxes," Forests, vol. 11, No. 9, Sep. 2020, pp. 961 (1-28).
Wang et al., "Removing Pectin and Lignin During Chemical Processing of Hemp for Textile Applications," Textile Research Journal, vol. 73, No. 8, Aug. 2003, pp. 664-669.
Wang, S., "Finding Your Fit. Finding Your Story.," MycoWorks Radio—Medium, Apr. 25, 2016, URL—https://medium.com/mycoworks-radio/finding-your-fit-finding-your-story-b2b4d960a6d1.
Waring et al., "Forests and Decarbonization—Roles of Natural and Planted Forests," Frontiers in Forests and Global Change, vol. 3, No. 58, May 2020, pp. 1-6.
Watanabe et al., "Micromorphological Features of Sclerotia Grains," Sclerotia Grains in Soils, Feb. 13, 2021, pp. 139-151.
Wieting et al., "Clearcut Carbon," A Sierra Club BC report on the future of forests in British Columbia, Dec. 2019, URL—https://sierraclub.bc.ca/wp-content/uploads/2019-Clearcut-Carbon-report.pdf.
Williams, J., "The Science and Technology of Composite Materials," Australian Academy of Science, Jun. 18, 2015, https://www.science.org.au/curious/technology-future/composite-materials.
World Meteorological Organization "WMO: New climate report is a clarion call for urgent action," Climate change, Aug. 9, 2021, URL—https://public.wmo.int/en/media/press-release/wmo-new-climate-report-clarion-call-urgent-action.
Yang et al., "Material Function of Mycelium-Based Bio-Composite: A Review," Frontiers in Materials, vol. 8, Sep. 30, 2021.
Yang et al., "Physical and Mechanical Properties of Fungal Mycelium-Based Biofoam," Journal of Materials in Civil Engineering, vol. 29, Mar. 2017.
Zhao et al., "Fungal Colonization and Biomineralization for Bioprotection of Concrete," Journal of Cleaner Production, vol. 330, Jan. 2022, pp. 129793.
Zhou et al., "Recent Advances in Microfluidic Devices for Bacteria and Fungus Research," TrAC Trends in Analytical Chemistry, vol. 112, Mar. 2019, pp. 175-195.
Zimele et al., "Novel Mycelium-Based Biocomposites (MBB) as Building Materials," Journal of Renewable Materials, vol. 8, No. 9, 2020, pp. 1067-1076.
"FAQs: Styrofoam—Children's Environmental Health Network," Children's Environmental Health Network, Apr. 5, 2021, Retrieved from https://cehn.org/our-work/eco-healthy-child-care/ehcc-faqs/faqs- styrofoamtm/.
"Fungal Futures—Growing Domestic Bio—Landscapes," Mar. 28, 2021, Retrievedd from http://www.fungal-futures.com/.
"Industrial Dynamics: A Major Breakthrough for Decision Makers," Harv. Bus. Rev., vol. 36, No. 4, 1958, pp. 37-66.
"Principles of Systems," Productivity, 1990.
"Why The Building Sector?," Architecture 2030, Jan. 3, 2022, URL—https://architecture2030.org/why-the-building-sector/.
Abdelhady et al., "Bio-Modules: Mycelium-Based Composites Forming a Modular Interlocking System through a Computational Design towards Sustainable Architecture," Designs, 2023, vol. 7, No. 1, Feb. 1, 2023, pp. 20 (1-17).
Abhijith et al., "Sustainable Packaging Applications from Mycelium to Substitute Polystyrene: A Review," Materials Today: Proceedings, vol. 5, No. 1, Feb. 3, 2018, pp. 2139-2145.
About Clearcutting | Sierra Club. https://www.sierraclub.org/california/cnrcc/stop-clearcutting-ca-about- clearcutting. Accessed Dec. 15, 2021.
Aleklett et al., "Build Your Own Soil: Exploring Microfluidics to Create Microbial Habitat Structures," The ISME Journal, vol. 12, No. 2, Nov. 14, 2017, pp. 312-319.
Ali et al., "Fungal Remediation of Cd( ii ) from Wastewater Using Immobilization Techniques," RSC Advances, vol. 11, No. 8, Jan. 25, 2021, pp. 4853-4863.
Amran et al., "Design Innovation, Efficiency and Applications of Structural Insulated Panels: A Review," Structures, vol. 27, Oct. 2020, pp. 1358-1379.
Anderson, N.,"Where Did Your House Grow?" Environmental Information Series, https://www.esf.edu/pubprog/house/default.htm. Accessed Jul. 21, 2021.
Appels et al., "Fabrication Factors Influencing Mechanical, Moisture- and Water-Related Properties of Mycelium-Based Composites," Materials & Design, vol. 161, Jan. 5, 2019, pp. 64-71.
Appels et al., "Mycelium Materials," Encyclopedia of Mycology, vol. 2, Jun. 1, 2021, pp. 710-718.
Architects Climate Action Network, "Preparation & Briefing—Stage 1 | ACAN | Circular Series," YouTube, URL—https://www.youtube.com/watch?v=Qy8kHWJ0VEw. Accessed Jul. 30, 2021.
Architects Climate Action Network, "Spatial Coordination—Stage 3 | ACAN | Circular Series," Jul. 30, 2021, YouTube, URL—https://www.youtube.com/watch?v=vERsBICVrB0.
Architects Climate Action Network, "Strategic Definition—Stage 0 | ACAN | Circular Series," Jul. 30, 2021, YouTube, URL—https://www.youtube.com/watch?v=tQDz4ArBOUA.
Asdrubali et al., "A Review of Unconventional Sustainable Building Insulation Materials," Sustainable Materials and Technologies, vol. 4, Jul. 29, 2015, pp. 1-17.
Attia, S., "Regenerative and Positive Impact Architecture: Learning from Case Studies," Springer Cham, 1st edition. 2018.
Attias et al., "Developing Novel Applications of Mycelium Based Bio-composite Materials for Design and Architecture," Conference: Building with bio-based materials: Best practice and performance specification, Sep. 2017, pp. 11.
Attias et al., "Mycelium Bio-Composites in Industrial Design and Architecture: Comparative Review and Experimental Analysis," Journal of Cleaner Production, vol. 246, Feb. 2020, pp. 119037.
Bai et al., "Assessment of SIP Buildings for Sustainable Development in Rural China Using AHP-Grey Correlation Analysis," Inter-

(56) References Cited

OTHER PUBLICATIONS national Journal of Environmental Research and Public Health, vol. 14, No. 11, Oct. 25, 2017, pp. 1292.
Bajwa et al., "Enhancement of Termite (*Reticulitermes flavipes* L.) Resistance in Mycelium Reinforced Biofiber-Composites," Industrial Crops and Products, vol. 107, Nov. 2017, pp. 420-426.
Bakis et al., "Fiber-Reinforced Polymer Composites for Construction-State-of-the-Art Review," Journal of Composites for Construction, vol. 6, No. 2, May 2002, pp. 73-87.
Baldwin et al., "Designing out Waste in High-Rise Residential Buildings: Analysis of Precasting Methods and Traditional Construction," Renewable Energy, vol. 34, No. 9, Sep. 2009, pp. 2067-2073.
Bartnicki-Garcia et al., "Evidence That Spitzenkörper Behavior Determines the Shape of a Fungal Hypha: A Test of the Hyphoid Model," Experimental Mycology, vol. 19, No. 2, Jun. 1995, pp. 153-159.
Bassilana et al., "External Signal-Mediated Polarized Growth in Fungi," Cell Architecture, vol. 62, Feb. 2020, pp. 150-158.
Bawden et al., "Hybrid Life Cycle Assessment of Low, Mid and High-Rise Multi-Family Dwellings," Challenges, vol. 6, No. 1, Apr. 2015, pp. 98-116.
Bergs et al., "Dynamics of Actin Cables in Polarized Growth of the Filamentous Fungus *Aspergillus nidulans*," Frontiers in Microbiology, vol. 7, 2016, pp. 682.
Berlik et al., "The Illusion of Preservation: A Global Environmental Argument for the Local Production of Natural Resources," Journal of Biogeography, vol. 29, No. 10-11, Oct. 2002, pp. 1557-1568.
Boehm et al., "State of Climate Action 2021: Systems Transformations Required to Limit Global Warming to 1.5° C.," World Resources Institute, Oct. 28, 2021, 249 Pages.
Boyer, M., "Philip Ross Molds Fast-Growing Fungi Into Mushroom Building Bricks That Are Stronger than Concrete," Inhabitate, Jun. 25, 2014, Retrieved from https://inhabitat.com/phillip-ross-molds-fast-growing-fungi-into-mushroom-building-bricks-that-are-stronger-than-concrete/.
Brand et al., "Mechanisms of Hypha Orientation of Fungi," Current Opinion in Microbiology, vol. 12, No. 4, Aug. 2009, pp. 350-357.
Bringing Embodied Carbon Upfront. World Green Building Council, Sep. 2019, p. 67, https://www.worldgbc.org/sites/default/files/WorldGBC_Bringing_Embodied_Carbon_Upfront.pdf.
Bulcke et al., "Three-Dimensional X-Ray Imaging and Analysis of Fungi on and in Wood," Microscopy and Microanalysis, vol. 15, No. 5, Oct. 2009, pp. 395-402.
Bumani et al., "Gypsum, Geopolymers, and Starch-Alternative Binders for Bio-Based Building Materials: A Review and Life-Cycle Assessment," Sustainability, vol. 12, No. 14, 2020, pp. 5666(1-20).
Canadian Hemp Trade Alliance, "Types of Hemp Fibre," Dec. 14, 2021, URL—https://www.hemptrade.ca/content.aspx?page_id=22&club_id=950211&module_id=409603.
Canales, K., "How Bolt ThBusiness Insider.Root-Derived Leather—Business Insider," May 19, 2018, Retrieved from https://www.businessinsider.com/bolt-threads-microsilk-mylo-spider-silk-sustainable-technology- fashion-2018-5.
Capra et al., "The Systems View of Life: A Unifying Vision," Cambridge University Press, Apr. 2014, Retrieved from https://www.cambridge.org/core/books/systems-view-of-life/35186BA5B12161E469C4224B6076ADFE.
Carrillo et al., "Biocomposites Using Waste Whole Chicken Feathers and Thermoplastic Matrices," Journal of Reinforced Plastics and Composites, vol. 32, No. 19, Oct. 2013, pp. 1419-1429.
Carroll, A., "Effect of Core Geometry and Size on Concrete Compressive Strength," Nov. 6, 2014, Retrievedd from https://etd.auburn.edu//handle/10415/4366.
Carvalho et al., "Modeling and Simulation of the Hot-Pressing Process in the Production of Medium Density Fiberboard (MDF)," Chemical Engineering Communications, vol. 170, No. 1, Jan. 1998, pp. 1-21.

Célino et al., "The Hygroscopic Behavior of Plant Fibers: A Review," Frontiers in Chemistry, vol. 1, No. 43, Jan. 24, 2014, pp. 1-12.
Cerimi et al., "Fungi as Source for New Bio-Based Materials: A Patent Review," Fungal Biology and Biotechnology, vol. 6, No. 1, Oct. 2019, p. 17, https://doi.org/10.1186/s40694-019-0080-y.
Chazdon et al., "The Potential for Species Conservation in Tropical Secondary Forests," Conservation Biology, vol. 23, No. 6, Dec. 2009, pp. 1406-1417.
Cherney et al., "Industrial Hemp in North America: Production, Politics and Potential," Agronomy, vol. 6, No. 4, 2016.
Chet et al., "Sclerotial Morphogenesis in Fungi," Annual Review of Phytopathology, vol. 13, No. 1, Sep. 1975, pp. 169-192.
Coletta et al., "Causal Loop Diagrams for Supporting Nature Based Solutions Participatory Design and Performance Assessment," Journal of Environmental Management, vol. 280, Feb. 2021, p. 111668.
Coley-Smith et al., "Survival and Germination of Fungal Sclerotia," Annual Review of Phytopathology, vol. 9, No. 1, Sep. 1971, pp. 65-92.
Corner, E. J. H., "A Fomes with Two Systems of Hyphae," Transactions of the British Mycological Society, vol. 17, No. 1-2, Aug. 1932, pp. 51-81.
Intro to Natural Materials | ACAN Natural Materials | ACAN. Directed by Architects Climate Action Network. YouTube, https://www.youtube.com/watch?v=oqSkp1SwgOA. Accessed Jul. 30, 2021.
Islam et al., "Mechanical Behavior of Mycelium-Based Particulate Composites," Journal of Materials Science, vol. 53, No. 24, Dec. 2018, pp. 16371-16382.
Islam et al., "Morphology and Mechanics of Fungal Mycelium," Scientific Reports, vol. 7, No. 1, Dec. 2017, pp. 13070.
IUCN "Forests and Climate Change," Nov. 11, 2017, Retrievedd from https://www.iucn.org/resources/issues-briefs/forests-and-climate-change.
Jacewicz, N.,"Making Furniture from Fungi," Scientific American, Dec. 15, 2015. Retrievedd from https://blogs.scientificamerican.com/guest-blog/making-furniture-from-fungi/.
Javadian et al., "Application of Mycelium-Bound Composite Materials in Construction Industry: A Short Review," SOJ Materials Science & Engineering, vol. 7, No. 2, Jan. 2020, pp. 1.
Javadian et al., "Mechanical Properties of Bamboo Through Measurement of Culm Physical Properties for Composite Fabrication of Structural Concrete Reinforcement," Frontiers in Materials, vol. 6, Feb. 2019, pp. 15.
Jiang et al., "Cost Modeling and Optimization of a Manufacturing System for Mycelium-Based Biocomposite Parts," Journal of Manufacturing Systems, vol. 41, Oct. 2016, pp. 8-20.
Jiang et al., "Manufacturing of Biocomposite Sandwich Structures Using Mycelium-Bound Cores and Preforms," Journal of Manufacturing Processes, vol. 28, Aug. 2017, pp. 50-59.
Jiang et al., "Non-destructive Observation of the Mycangia of Euwallacea Interjectus (Blandford) (Coleoptera: Curculionidae: Scolytinae) Using X-ray Computed Tomography," Entomological Science, vol. 22, No. 2, Jun. 2019, pp. 173-181.
Jones et al., "Agricultural By-Product Suitability for the Production of Chitinous Composites and Nanofibers Utilising Trametes Versicolor and Polyporus Brumalis Mycelial Growth," Process Biochemistry, vol. 80, May 2019, p. 95?
Jones et al., "Inherent Species Characteristic Influence and Growth Performance Assessment for Mycelium Composite Applications," Advanced Materials Letters, vol. 9, Jan. 2018, pp. 71-80.
Jones et al., "Mycelium Composites: A Review of Engineering Characteristics and Growth Kinetics," Journal of Bionanoscience, vol. 11, No. 4, Aug. 2017, pp. 241-257.
Jones et al., "Thermal Degradation and Fire Properties of Fungal Mycelium and Mycelium—Biomass Composite Materials," Scientific Reports, vol. 8, No. 1, Dec. 2018, pp. 17583.
Jones et al., "Waste-Derived Low-Cost Mycelium Composite Construction Materials with Improved Fire Safety," Fire and Materials, May 2018, pp. 816-825.
Jones et al., "Waste-Derived Low-Cost Mycelium Nanopapers with Tunable Mechanical and Surface Properties," Biomacromolecules, vol. 20, No. 9, Sep. 2019, pp. 3513-3523.

(56) References Cited

OTHER PUBLICATIONS

Jones, N., "Peak Timber," Nature Climate Change, vol. 2, No. 3, Mar. 2012, pp. 141-141.
Joubert et al., "Parasitic Green Algae," Annual Review of Phytopathology, vol. 9, No. 1, Sep. 1971, pp. 45-64.
Kallio et al., "Sequester or Substitute—Consequences of Increased Production of Wood Based Energy on the Carbon Balance in Finland," Journal of Forest Economics, vol. 19, No. 4, Dec. 2013, pp. 402-415.
Khaliq et al., "Industrial Application Of Psyllium: An Overview," ACTA Universitatis Cibiniensis, vol. 67, No. 1, Sep. 2015, pp. 210-214.
Kidalova et al., "Utilization of Alternative Materials in Lightweight Composites," Journal of Cleaner Production, vol. 34, Oct. 2012, pp. 116-119.
King, B. "Restore Mushroom Packaging in the Sweet Spot of Price, Performance and Sustainability," New Equipment Digest, Mar. 15, 2013, Retrievedd from https://www.newequipment.com/research-and-development/article/22058396/restore-mushroom-packaging-in-the-sweet-spot-of-price-performance-and-sustainability.
Kostic et al., "Quality of Chemically Modified Hemp Fibers," Bioresource Technology, vol. 99, No. 1, Jan. 2008, pp. 94-99.
Law et al., "Land Use Strategies to Mitigate Climate Change in Carbon Dense Temperate Forests," Proceedings of the National Academy of Sciences, vol. 115, No. 14, Apr. 2018, pp. 3663-3668.
Le Troëdec et al., "Influence of Chemical Treatments on Adhesion Properties of Hemp Fibres," Journal of Colloid and Interface Science, vol. 356, No. 1, Apr. 2011, pp. 303-310.
Le Troëdec et al., "Influence of Various Chemical Treatments on the Interactions between Hemp Fibres and a Lime Matrix," Journal of the European Ceramic Society, vol. 29, No. 10, Jul. 2009, pp. 1861-1868.
Leblanc, R., "The Importance of Wood Recycling in C&D Management—Wood Recycling in the Construction Waste Stream," Small Business, Nov. 26, 2018, URL—https://www.thebalancesmb.com/wood-recycling-construction-2877760.
Lelivelt, R. J. J. The Mechanical Possibilities of Mycelium Materials. Eindhoven University of Technology, Mar. 2, 2015, https://research.tue.nl/en/studentTheses/the-mechanical-possibilities-of-mycelium-materials.
Lionetto et al., "Monitoring Wood Degradation during Weathering by Cellulose Crystallinity," Materials, vol. 5, No. 10, Oct. 2012, pp. 1910-1922.
Lodge et al., "Effects of Hurricane-Felled Tree Trunks on Soil Carbon, Nitrogen, Microbial Biomass, and Root Length in a Wet Tropical Forest," Forests, vol. 7, 2016, pp. 264.
Lu et al.,"Thermal Stability and Thermo-Mechanical Properties of Hemp-High Density Polyethylene Composites: Effect of Two Different Chemical Modifications," Composites Part B: Engineering, vol. 44, No. 1, Jan. 2013, pp. 484-490.
Lüthi et al., "High-Resolution Carbon Dioxide Concentration Record 650,000-800,000 Years before Present," Nature, vol. 453, No. 7193, May 2008, pp. 379-382.
Ma et al., "Fungal Surface Remodelling Visualized by Atomic Force Microscopy," Mycological Research, vol. 110, No. 8, Aug. 2006, pp. 879-886.
Madelin, M. F., "Visible Changes in the Vegetative Mycelium of Coprinus Lagopus Fr. at the Time of Fruiting," Transactions of the British Mycological Society, vol. 43, No. 1, Mar. 1960, pp. 105-110, IN5.
Madsen et al., "Hemp Yarn Reinforced Composites—I. Yarn Characteristics," Composites Part A: Applied Science and Manufacturing, vol. 38, No. 10, Oct. 2007, pp. 2194-2203.
Mafla-Endara et al., "Microfluidic Chips Provide Visual Access to in Situ Soil Ecology," Communications Biology, vol. 4, No. 1, Dec. 2021, pp. 889.
Magwood, C., "Opportunities for Carbon Dioxide Removal and Storage in Building Materials," Trent University, Sep. 2019. URL—https://www.chrismagwood.ca/uploads/1/5/9/3/15931000/magwood_opportunities_for_co2_capture_and_storage_in_building_materials_copy.pdf.
Mahendra et al., "Towards a More Equal City: Seven Transformations for More Equitable and Sustainable Cities," World Resources Institute, 2021.
Manan et al., "Synthesis and Applications of Fungal Mycelium-Based Advanced Functional Materials," Journal of Bioresources and Bioproducts, vol. 6, No. 1, Feb. 2021, pp. 1-10.
Mang et al., "Regenerative Development and Design: A Framework for Evolving Sustainability," Wiley, 2016.
Maxwell et al., "Degradation and Forgone Removals Increase the Carbon Impact of Intact Forest Loss by 626%," Science Advances, vol. 5, No. 10, Oct. 2019.
Mbabali et al., "Development of Rice Husk and Sawdust Mycelium-Based Bio-Composites: Optimization of Mechanical, Physical and Thermal Properties," Journal of The Institution of Engineers (India): Series D, Feb. 2023.
Meadows et al., "The Limits To Growth," A Report For The Club Of Rome's Project On The Predicament Of Mankind. Universe Books, 1972.
Melia R, "Everything You Own Could One Day Be Made from Mushrooms," Business Insider, Jul. 14, 2016, URL—https://www.businessinsider.com/mycoworks-2016-7. Accessed Apr. 10, 2020.
Melton, P., "The Urgency of Embodied Carbon and What You Can Do about It," Dec. 16, 2021, URL—https://www.buildinggreen.com/feature/urgency-embodied-carbon-and-what-you-can-do-about-it.
Meyer et al., "Growing a Circular Economy with Fungal Biotechnology: A White Paper," Fungal Biology and Biotechnology, vol. 7, No. 1, Dec. 2020, pp. 5.
Miller et al., "Greenhouse Gas Emissions from Concrete Can Be Reduced by Using Mix Proportions, Geometric Aspects, and Age as Design Factors," Environmental Research Letters, vol. 10, No. 11, Nov. 2015, pp. 114017 (1-12).
Millet et al., "Increasing Access to Microfluidics for Studying Fungi and Other Branched Biological Structures," Fungal Biology and Biotechnology, vol. 6, No. 8, Dec. 2019, pp. 1-12.
Modern Meadow, "Our Technology," Apr. 10, 2020, Retrievedd from www.modernmeadow.com, http://www.modernmeadow.com/our-technology/.
Montford et al., "A Comparison of the Biodiversity Friendliness of Crops with Special Reference to Hemp (*Cannabis sativa* L.)," Journal of the International Hemp Association, vol. 6, No. 2, Dec. 1999, pp. 53-63.

\* cited by examiner

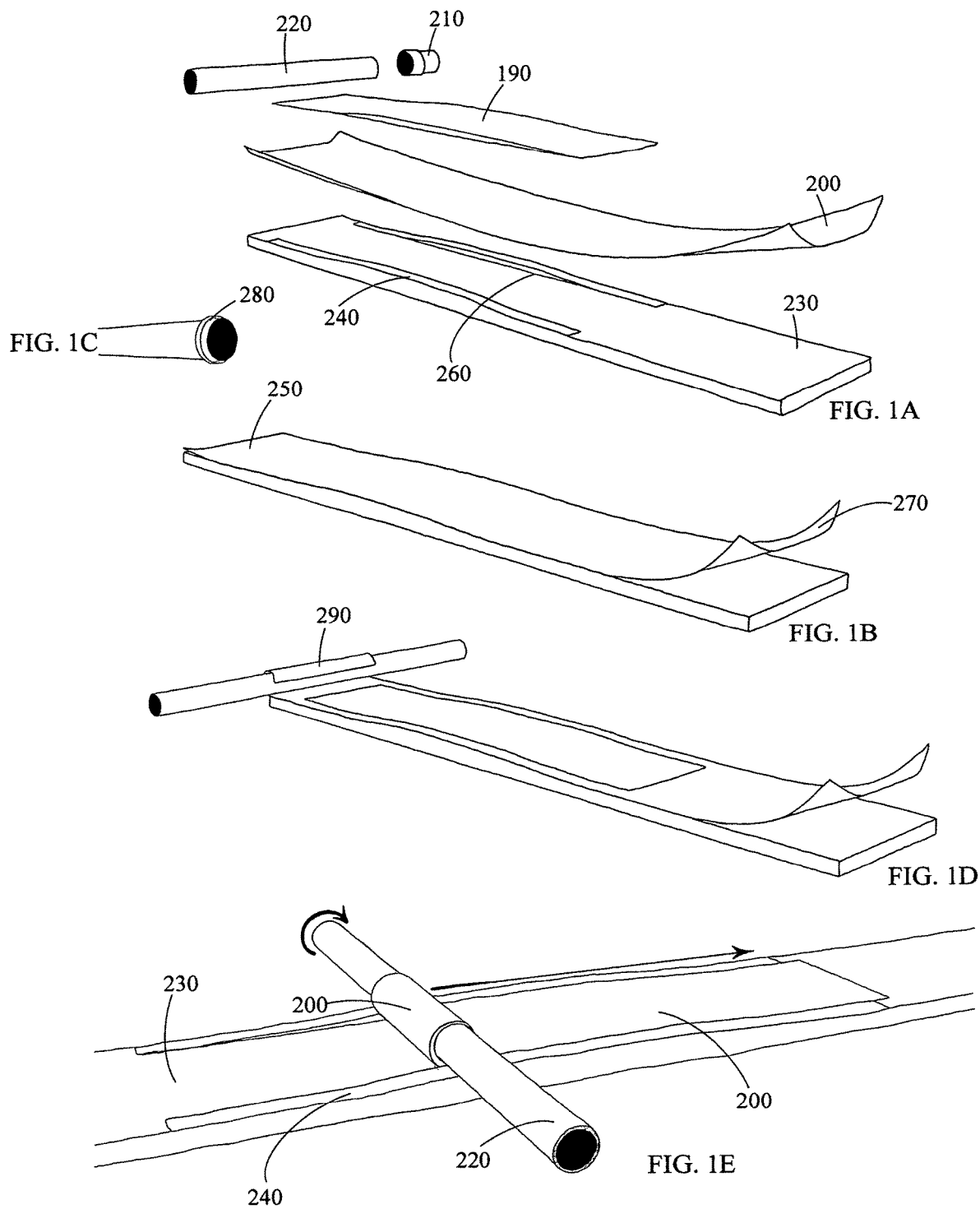

Process Flow Chart

901. Measure, cut, pour, prepare

901.1. Inoculated substrate 190

901.1.1. Fungal Species
- 901.1.1.1. Select appropriate fungal organism(s)
- 901.1.1.2. Determine appropriate inoculation method

901.1.2. Inoculated substrate 190
- 901.1.2.1. Select appropriate inoculated substrate 190 type and particle size
- 901.1.2.2. Determine appropriate inoculation method

901.1.3. Admix
- 901.1.3.1. Select appropriate admix nutrients to achieve desired density and hyphal phenotypical expression
- 901.1.3.2. Measure admix components and prepare as necessary

901.2. Internal textile 200
- 901.2.1. Select appropriate weave and weight of internal textile 200
- 901.2.2. Determine appropriate sterilization/pasteurization method
- 901.2.3. Sterilize/pasteurize internal textile 200

901.3. Stockinette 210/external textile (fascia)
- 901.3.1. Select appropriate weave and weight of stockinette 210 textile
- 901.3.2. Determine appropriate sterilization/pasteurization method method
- 901.3.3. Sterilize/pasteurize stockinette 210 textile

902. Tools, molds, chambers

902.1. Inverted mold tool 220
- 902.1.1. Select appropriate material, profile rail 240, and dimensions for inverted mold tool 220

FIG. 2A 902.1.2. Using aseptic technique, cleanse all surfaces of inverted mold tool 220

902.2. Inoculated substrate 190, template 230, and profile rails 240

902.2.1. Determine size and dimensions of Inoculated substrate 190, template 230

902.2.2. Create profile rail 240 for desired final geometry 902.2.3. Construct inoculated substrate 190, template 230, with profile rails 240 at appropriate distance apart for desired final geometry

902.3. Mixing bin 902.3.1. Ensure mixing bin is cleaned with aseptic technique 902.3.2. Ensure mixing tools are cleaned with aseptic technique

902.4. Fermentation chamber 902.4.1. Fermentation chamber can be any room or box that is capable of maintaining adequate spacing of fermenting parts and where the environmental controls of the desired fungal ecology can be regeneratively maintained 902.4.2. Ensure surfaces of fermentation chamber are cleaned with aseptic technique 902.4.3. Ensure environmental controls for fermentation are operable and set at desired levels 902.4.4. Ensure racks, hooks, other items used in fermentation chamber are adequately cleaned with aseptic technique

902.5. Grow pod 902.5.1. The grow pod is intended to be a reusable skin that is stretched around the exterior surface 340 at a pre-determined time in the fermentation sequence. This sudden contact with a non-breathable surface initiates a phenotypic change in the growth efforts of the fungal mycelium. The disruption of mycelial primordia on the exterior surface 340 of the finished part 300 inhibits the further maturation of fruiting bodies and encourages strong, anastomosed growth of mycelium to proliferate across the textile pore spaces that

FIG. 2B are devoid of mycelium that are still remaining in the exterior surface 340

902.5.2. Ensure grow pod surfaces are cleaned with aseptic technique 902.5.3. Ensure grow pods are stored for later use in aseptic manner

902.6. Dehydration unit 902.6.1. The dehydration unit can be composed of a simple box that allows for a constrained airflow to be directed over appropriately spaced parts at a desired temperature.

902.6.2. Ensure dehydration unit controls are operable 902.6.3. Ensure that desired dehydration settings are achievable 902.6.4. Ensure that there is sufficient room for finished parts with adequate air flow

903. Prepare Inoculated substrate 190, template 230, and inverted mold tool 220 for filling

903.1. Layout pasteurized internal textile 200 onto Inoculated substrate 190, template 230, 903.1.1. allow overlay of at least 25 mm over profile rails 240

903.1.2. allow enough excess internal textile 200 to form at least one full turn 250 around inverted mold tool 220 at start 903.1.3. tuck into corners of template profile rail 240 edge 260 that is perpendicular to face of filling template bed 903.1.4. allow enough excess internal textile 200 to form at least one full turn around 270 inverted mold tool 220 at end of rolling procedure 903.1.5. spray with $H_2O_2$

903.2. Prepare inverted mold tool 220

903.2.1. layer with stockinette 210

903.2.2. tuck away excess 280 stockinette 210 for use later as covering to become exterior fascia 903.2.3. spray stockinette 210 with $H_2O_2$

FIG. 2C

903.3. Lay inoculated inoculated substrate 190 onto template

- 903.3.1. covering the internal textile 200 1.3
- 903.3.2. placing more mass in areas of higher profile
- 903.3.3. Inoculated substrate 190 should not be compacted at this point
- 903.3.4. Inoculated substrate 190 should be uniformly laid onto the template 230 in accordance with the profile rail 240

903.4. Compact Inoculated substrate 190 to suitable, pre-determined density

903.5. Lay over excess 3.1.1 internal textile 200 1.3 along edge of template rail

- 903.5.1. Stockinette 210 should be evenly compacted along rail edge
- 903.5.2. Internal textile 200 should not bunch
- 903.5.3. Spray inoculated inoculated substrate 190 with $H_2O_2$

904. Create part

904.1. Roll up part onto inverted mold tool 220

- 904.1.1. Roll starting with the excess internal textile 200 onto prepared inverted mold tool 220
- 904.1.2. Begin rolling internal textile 200 and inoculated substrate 190 onto inverted mold tool 220 ensuring density is maintained
- 904.1.3. Finish by rolling excess internal textile 200 over the part
- 904.1.4. Ensure cloth is not bunched
- 904.1.5. Spray with $H_2O_2$

904.2. Overlay external fascia

- 904.2.1. Ensure external fascia is covering rolled part with sufficient compression
- 904.2.2. Dress ends of fascia to ensure adhesion with rest of part (best attached using the pressure from the inverted mold tool 220) and to ensure manifold surface

FIG. 2D

904.3. Use tooling (if desired) to create final geometries
- 904.3.1. admix should be of appropriate makeup to allow for plasticity
- 904.3.2. brief compression into tooling is all that is required to achieve desired geometries such as flat face sections
- 904.3.3. spray assembly with $H_2O_2$

905. Fermentation process

905.1. Place whole assembly into aseptic fermentation chamber
- 905.1.1. set temp to between 22-26 celsius
- 905.1.2. set RH to 85%-100%
- 905.1.3. ensure low to moderate, filtered air flow
- 905.1.4. ferment for 48 hours
- 905.1.5. spray whole part with fine mist of $H_2O_2$ every 12 hours

905.2. Optionally, during early fermentation, parts are still plastic, and further geometry can be pressed into the parts

905.3. Place growth pod over whole assembly
- 905.3.1. spray whole part with fine mist of $H_2O_2$
- 905.3.2. allow minimal air flow
- 905.3.3. increase $CO_2$ concentrations
- 905.3.4. decrease RH to 65%-75%, allow organism to regulate humidity
- 905.3.5. ferment for additional 24 hours

905.4. Remove growth pod
- 905.4.1. spray whole part with fine mist of $H_2O_2$
- 905.4.2. increase RH to 85%-100%
- 905.4.3. ferment for additional 24-48 hours depending on part size (may be up to an additional 14 days)
- 905.4.4. spray whole part with fine mist of $H_2O_2$ every 12 hours

FIG. 2E

906. Create superstructures

To create larger superstructures that are adhered together with mycelium, combine part faces to be joined together before drying to ensure that organism can proliferate through the disparate parts to create a larger whole.

907. Drying

907.1. Begin to air dry part
907.1.1. before drying spray whole part with fine mist of $H_2O_2$
907.1.2. decrease RH to below 40%
907.1.3. increase air temp to 32-42 celsius
907.1.4. increase filtered air flow to improve drying
907.1.5. dry for 24 hours

907.2. Place in heated drying chamber
907.2.1. temp suitable to permanently terminate organism growth (> 75 celsius)
907.2.2. ensure rapid air flow
907.2.3. ensure moisture content is < 35% at end of drying process

907.3. Part is now ready for use in structural applications

FIG. 2F

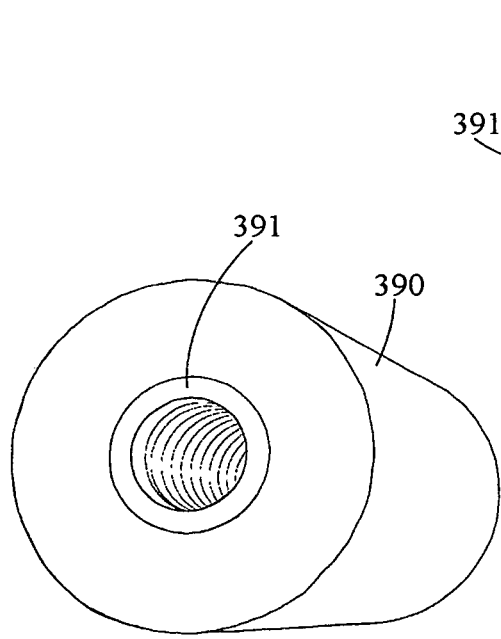
FIG. 5A
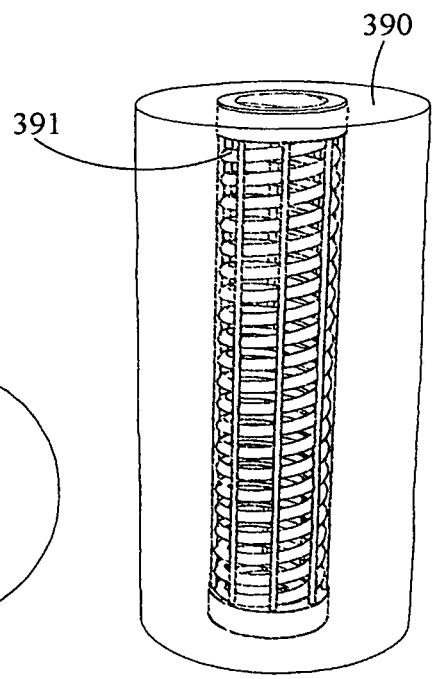
FIG. 5B
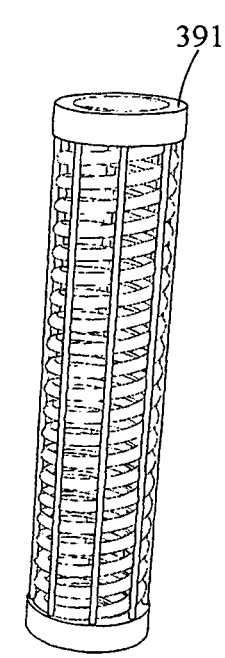
FIG. 5C
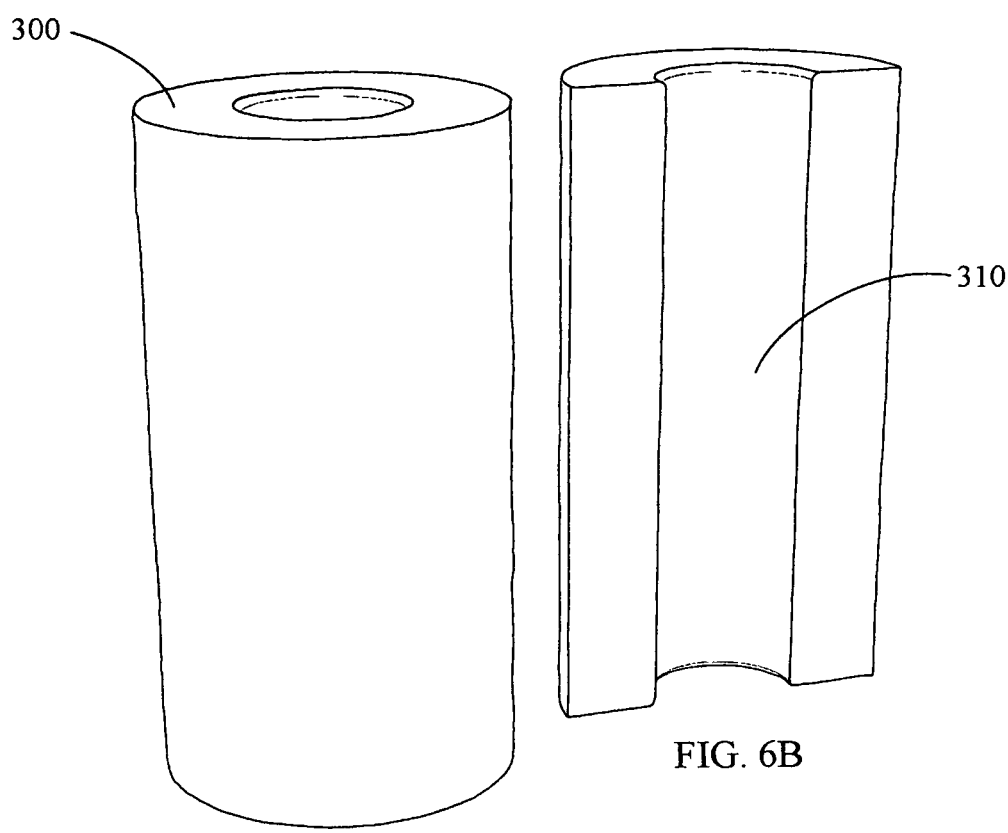
FIG. 6A
FIG. 6B

METHOD FOR CREATING A STIFF, RIGID MYCELIUM-BASED BIOCOMPOSITE MATERIAL FOR USE IN STRUCTURAL AND NON-STRUCTURAL APPLICATIONS

BACKGROUND OF THE INVENTION

Humanity faces several impending existential threats. Our atmosphere is being choked, in part, by shrinking forests, which in turn has a deleterious effect on biodiversity. Our oceans and wild places are not immune from the spurious legacy of plastics. Our watersheds are tainted with the bitter repercussions of an over-reliance on "better living through chemistry." Our technological innovations rely on insanely intricate supply chains where raw materials criss-cross the globe several times before making their way into a final product. Our cycles of extraction and production are unsustainable. Our current rate of extraction of timber from our forests will result in a complete desolation of these vital habitats within a generation.

By facing these threats head on, we can avoid passing the point of no return. We still have time to change our methods of design and manufacture to ensure that we can restore our balance with the rest of the biosphere. Finding inspiration from natural, biological processes can usher in a new generation of truly regenerative building materials that can help humanity to slough off the old cycles of extraction, manufacture, and disposal.

Fungi have a unique ability to rapidly self-replicate through a variety of substrata through the apical branching of its vegetative body known as mycelium. On the molecular level, the hyphae (the sub-unit of fungal mycelium) form adhesive bonds with virtually all substrata that it may come in contact with.

With respect to the various candidate species that one would use in creating mycelium-based biocomposites—mycelium of the filamentous fungi types that are preferentially attracted to substrata with a higher lignin content (~20% lignin) are of particular interest. These types are also attracted to hemicellulose and cellulose, One could tune the species chosen to the desired traits that particular species will exhibit given a set of environmental criteria known as fungal ecology. Specifically, fungal ecology herein refers to the tuning and control of relative humidity (RH), ambient temperature, and air gas mixture. Mycelium will explore its surroundings in search of both nutrients and structure. By tuning these characteristics, mycelium can provide a robust matrix for a composite material.

Prior art describe methods to create composite materials from a substrate (reinforcement) and mycelium (matrix) or to create pure mycelium materials (e.g., U.S. Pat. Nos. 9,485,917, 9,410,116, 9,803,171, 8,298.809, and 8,999,687, 10,589,489, 10,154,627, 9,914,906, 10,144,149). Since those filings, a better understanding of the impacts of certain tunable aspects of mycelium have given rise to an improved method for creating composite materials that can serve in structural/load-bearing capacities.

Especially in terms of:
Application of fungal ecology to produce more vigorous mycelium growth
Increased density
More consistency in mycelium growth
Inversion of mold tool surface contact
Enhances organism's ability to self-regulate gas exchange with room air
Reduces exogenous inputs necessary to produce stronger parts
Improves ability to regulate moisture
Improves ability to mitigate infection
Introduction of hollow sections with manifold surfaces to produce lighter parts with improved rigidity and strength profiles
Exterior and interior surfaces that provide nano-structural scaffolding for mycelial growth
Optimization of substrate mass and surface area needed to produce load bearing parts In spite of more than a decade of exposure for mycelium composites and materials in the marketplace, the consensus among researchers and industry analysts had previously (and still currently) maintained that there was a gap in capabilities for mycelium composites. Peer-reviewed articles, written to date, have articulated the need for further exploration into methods that can produce load-bearing parts from mycelium. Some publications have relegated mycelium composites to non-structural applications.

In light of the present invention, it is now known that rigid composites are achievable with structural/load-bearing characteristics (as well as surface hardness and screw hold). The method described herein is one such method that improves upon prior art. Key improvements include:
Improving on the limitations of using rigid enclosures
Moisture handling
Infection control
Proliferation of mycelium
Gas exchange
Better understanding of the impact of $O_2$ and $CO_2$ on the heterogeneity of hyphal morphology
Better understanding of the need to vary fungal ecological conditions throughout the fermentation process in order to promote proper mix of different hyphal morphologies
Elimination of the need for multiple fermentation steps to create structural parts
Elimination of the need for adhesives and/or heat and pressure to create functional densities
Identification of low-tech methods for producing functional parts for use in various industries

BRIEF SUMMARY OF THE INVENTION

One aspect of the present invention includes a specific enclosure type derived from fabric forming using a textile constituted in stockinette (or similar) form with a specific yarn type, warp and weft, and weave density designed to promote gas exchange and moisture retention to produce a mycelium-based biocomposite part with a certain set of desired physical characteristics and mechanical capabilities. The stockinette provides low, constant, evenly applied external pressure to the substrate which serves to provide biological cues to the fungal organism that promotes heterogenous hyphal morphologies that are beneficial to creating rigid structures with sufficient surface hardness to serve in structural, load-bearing applications. The simplified, streamlined drying method described in the present invention results in a part that has functional, structural characteristics without further post-processing steps as necessary in prior art.

Another aspect of the present invention describes a method that allows for the fermentation of parts within a fabric formed enclosure that promotes an advantageous combination of hyphal morphologies. Specifically, the fabric formed enclosure is shaped to form a manifold surface. The manifold surface is enhanced by an inverted, internal mold tool. By inverting the position of the mold tool, gas exchange is improved. Gas exchange is best regulated by the organism. The self-regulation of gas exchange promotes heterogenous hyphal morphological expression throughout the thickness of the wall section as the hyphae respond to the gradient of gases in the room air. This heterogenous hyphal morphology enhances the physical characteristics and mechanical capabilities of the part. The manifold surface necessitates the creation of a hollow section when viewed perpendicular to the long axis. This hollow section provides a reduced volume within which the mycelium need to colonize. A reduced volume means there is a commensurate reduction in the time necessary for the organism to fully colonize the substrate. This reduction in time to full colonization has multiple other advantages, namely commensurate reductions in:

Time to manufacture

Opportunistic infection rates

These and other advantageous reductions create improvements in the mechanical performance of the finished parts.

Yet another aspect of the present invention includes an encompassing external skin that forms a manifold surface to the composite material made from any useful textile. The water retention of the chosen yarn as well as the warp and weft of the weave also serves to help regulate moisture levels throughout the fermenting part. The external skin also produces a light amount of pressure (less than 15 mmHg) which signals the branching hyphae to produce a tunable mix of hyphal morphologies which organize across the external surface of the finished part.

Yet another aspect of the present invention is an introduction of a tunable blend of admixes that can help to increase or decrease final density (depending on desired performance). The admixes will be favorably derived from regenerative, organic or inorganic materials (though a nearly inexhaustible list of admix components can be utilized). By tuning the nutrient content, discreet particle size, and mechanical characteristics of the admix components, the hyphal matrix can create a wide array of performance characteristics in conjunction with the substrate. This admix blend, matched with the previously mentioned, tunable aspects of the present invention, can eliminate the need for costly machine tooling needed to compress the mycelium composite pre or post-fermentation. This reduces complexity in manufacture, producing a stronger part with fewer mechanical inputs using regeneratively sourced and inexpensive components.

Yet another useful aspect of the present invention is an improved ability to form larger, structural members from various, discreet parts made with the same or varying methods of manufacture. Coupling parts together during fermentation will result in a superstructure that has synergistic improvements in strength and durability than the parts would have individually. That superstructure will have the advantage of bonding through the external textile skin vis a vis the inherent adhesive qualities of mycelium, which produce incredibly strong adhesion wherever adequate pressure (around 10 mmHg or greater) presses the disparate parts together. This eliminates the need to use adhesives when forming larger, structural parts like architectural headers or joists. The simplification in production processes allows for a wider application of the material at a lower cost to manufacture.

BRIEF DESCRIPTION OF THE SEVERAL VIEWS OF THE DRAWING

FIGS. 1A-1E Pre-forming option—roller table

FIG. 1A—Top perspective, exploded view of the components involved in the process described in FIGS. 2A-2F FIG. 1B—Top perspective view showing the internal textile after it is lowered into place on top of the filling template FIG. 1C—Perspective view showing the stockinette being prepared onto the inverted mold tool FIG. 1D—Shows a top perspective view of the roller table with the inverted mold tool in place ready to begin forming the final part with one full turn of internal textile pre-wrapped around the inverted mold tool FIG. 1E—Top perspective that shows the manner in which the inner textile and the inoculated substrate are rolled together FIGS. 2A-2F—Process Flow Chart***—One embodiment of a step by step process to create structural, rigid mycelium-based biocomposite parts FIGS. 3A-3C—Layer adhesion—cut away FIG. 3A—Top perspective of one embodiment of the present invention after the fermentation process has finished FIG. 3B—Top perspective of the embodiment from FIGS. 2A-2F with the inverted mold tool removed and after the drying process has been completed FIG. 3C—Top perspective view of a cross-sectioned part. The view depicts the way the internal textile forms several layers of support for the final part's internal structure FIGS. 4A-4B Post-forming option FIG. 4A—Perspective view of one embodiment for providing a way to incorporate more complex geometry into the part pre-fermentation or in the early stages of fermentation while the material is still plastic FIG. 4B—Perspective view of an embodiment of a forming tool from 4A with the part removed after the geometry has been imbued into the part FIGS. 5A-5C—Augmented support FIG. 5A—Perspective view of a finished part showing the placement for the internal support structure along the long axis FIG. 5B—Perspective view of the finished part with an internal view of the support structure FIG. 5C—Perspective view of the internal support structure before placement inside the part FIGS. 6A-6B—Hollow cylinder FIG. 6A—Perspective view of a finished part showing a finished part without any augmented support.

FIG. 6B—Perspective view of the finished part with a cross-sectional view of the interior surface of the part. The view depicts the Riemannian manifold surface that is achieved with the process described in FIGS. 2A-2F FIGS. 7A-7B—Partially filled cylinder FIG. 7A—Perspective view of a finished part showing the placement for composite material used as support plugs in each end of a finished part, partially filling the internal void for added support FIG. 7B—Perspective view of the finished part with a cross-sectional view of the plugs as they interface with the internal surface of the part.

FIG. 8A—Perspective view of a finished part showing the placement for composite material used as a support plug running through the entire length of the internal void of a finished part, fully filling the internal void for added support FIG. 8B—Perspective view of the finished part with a cross-sectional view of the plug as it interfaces with the internal surface of the part FIGS. 9A-9F Different final geometry options FIG. 9A—Top perspective of a basic, preferred embodiment of the present invention FIG. 9B—Top perspective view of another embodiment of the present invention with several faces having been pressed into the part to form a hexagonal profile to the finished part FIG. 9C—Perspective view of another embodiment of the present invention where several parts with the same geometry as in FIG. 9B joined together along faces that are adhered together with the mycelial matrix to form a small structural support column FIG. 9D—Shows a top perspective view of another embodiment of the present invention where tubes with a triangular profile have been adhered together by mycelial matrix to form a larger, structural support column FIG. 9E—Top perspective view of another embodiment of the present invention where several tubes with a rectangular profile are adhered together by mycelial matrix to form a corner support structure FIG. 9F—Top perspective view of another embodiment of the present invention where several tubes with a rectangular profile are adhered together by mycelial matrix to form a structural beam

DETAILED DESCRIPTION OF THE INVENTION

Figures 3A, 3B, 3C:
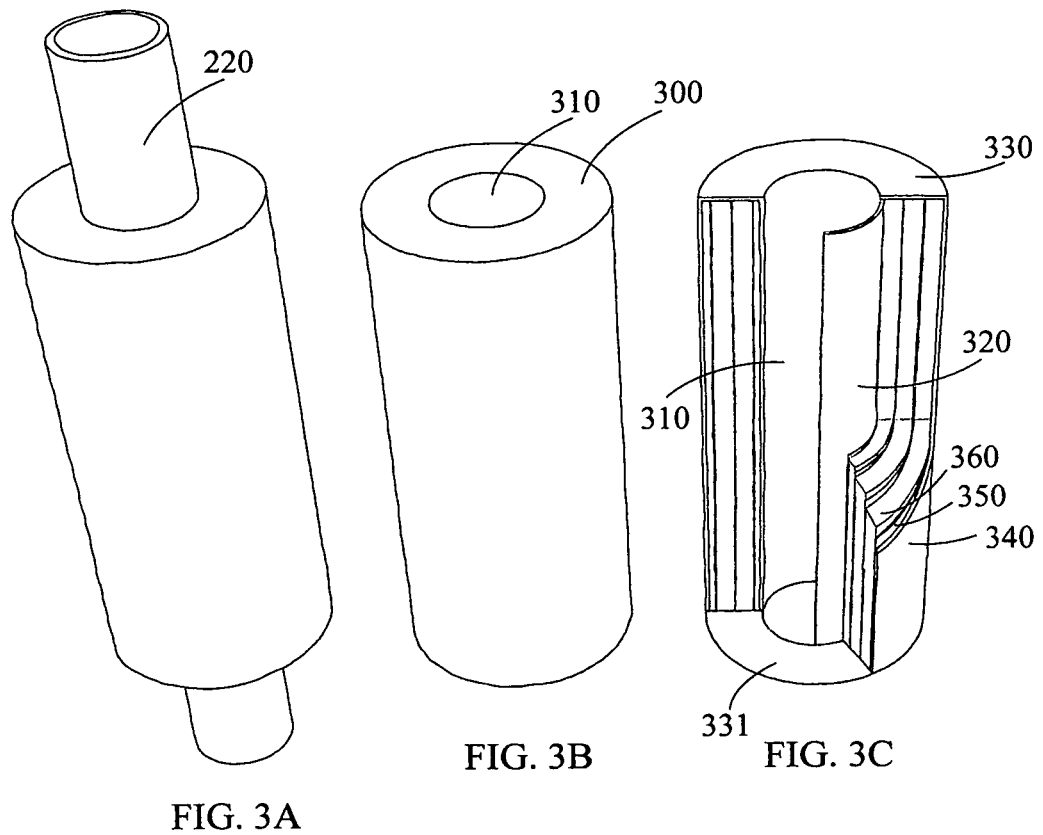

The potential of mycelium-based biocomposites to have a positive impact in the fight against anthropogenic climate change cannot be overstated. Finding sectors where unadulterated biological/plant/fungus based materials can replace non-regenerative materials is a vital task of the next several generations. Mycelium-based biocomposites will play a large role in new generations of natural, regenerative materials due to their diverse endpoints with a seemingly endless gradient of characteristics and capabilities based on a seemingly endless array of fungal ecology combinations available now and in the future. By replacing harmful incumbent product classes, mycelium-based biocomposite materials can even contribute to the long-term sequestration of carbon atoms when used as a building material.

A large number of materials in use today are composites. That is, they are materials derived from two or more distinct materials with vastly different physical characteristics and mechanical capabilities that, when physically combined (chemical solutions do not fit this definition), create a new material with vastly superior physical characteristics and mechanical capabilities. There are two basic components of a composite material:

1. Matrix
2. Reinforcement

The matrix is typically an adhesive type of material such as resin. The strength of the composite material relies heavily on the ability of the matrix to form a strong bond between the structural elements of the composite. The reinforcement of a composite can come in myriad forms, but some common forms include sand, woven textiles, wood chips, and similar materials that can be uniformly compacted and subsequently uniformly coated by the matrix. The result being a material that maintains the original mass of the constituent components.

In a mycelium based biocomposite material, the mycelium act as the matrix, while the substrate becomes the structural component of the composite. There are two main distinguishing features between the present invention and prior art. The first, is that prior art describe using lamination of mycelium composites to exogenous structures that are already rigid, with structural capabilities. Prior art describe these structures as being laminated to the mycelium composite using traditional adhesives. Another method described in prior art is growing the mycelium in direct contact with the structural material to allow the mycelium to attach to the structure without additional adhesives. While these methods will result in a material that is able to be used in structural applications, it is not by the contribution or capability of the mycelium biocomposite itself, but solely in the capabilities of the exogenous, structural components alone. The addition or subtraction of mycelium in these instances (and as described in prior art) will not change the nature of the structural capability of the exogenous input. The present invention differs in that it describes a process wherein the final part itself displays self-supporting structural capabilities that are vastly superior to prior art. The present invention does not require the finished part to be mechanically or chemically fastened to an exogenous framework in order to serve in a load-bearing fashion.

The second, main distinguishing factor for the present invention is that prior art describe methods that require large amounts of industrial pressure (exceeding 10 psi to upwards of 5000 psi) to post-process parts that can serve in rigid applications. Prior art describe this pressure being augmented by excessive temperatures (300° F.-600° F.) being applied concurrent with the compression for several hours at a time (4-24 hours). The promise of mycelium-based biocomposites is their handsome carbon profiles. When a manufacturing process requires large tooling for compression and/or heat, there are unfortunate and exponential increases in the embodied carbon of that process.

The ability to update the geometry and scale of a process that relies on industrial compression and heat is both limited and cost prohibitive. Furthermore, and perhaps most importantly, reliance on industrial compression results in a dramatic increase in the amount of substrate material required to create a strong part. Prior art describe compressing the material down to ⅓ or less of the original thickness before compression. This 3-fold increase in substrate demand would be cost prohibitive at scale.

Current understanding of the growth characteristics of fungal mycelium describe a morphological advantage to providing pressure during the growth process. By exploiting these biological characteristics, the present invention is able to use far lower amounts of pressure (less than 15 mmHg or 0.3 psi) that are more conducive to promote the nano-structural capabilities inherent in mycelium. Prior art's reliance on industrial, post-fermentation compression can actually serve to break these beneficial nano-structural bonds. The result of prior art's described methods is that the compressed biocomposite's inherent qualities are rendered inconsequential and instead replaced with a material that is held strongly together by virtue of the mechanical compression and/or infused resins.

As with lamination to stronger materials described in prior art, the compression described in prior art speak more to the effectiveness of the compressive process than the characteristics and capabilities of the material itself. The present invention describes a process that results in the growth of parts that far surpass the mechanical capabilities of prior art using a very minute fraction of the embodied carbon. In fact, to achieve stronger parts, the present invention has no reliance on mechanical compression at any stage, other than that supplied by the constituent fascia described in the present invention's composition. This reduction in mechanical inputs and raw materials over prior art has a commensurate reduction in cost and complexity of manufacture.

An important consideration in the commercial applications for any material is scalability. Both in terms of the material's physical mass and volume at commercial scale and in terms of number of units that can be produced at that same scale. As previously detailed, the reliance on compression and/or heat of prior art creates cost considerations that are amplified at commercial scale. Equally impactful to scaling is prior art's reliance on lamination to exogenous, structural components. The addition of exogenous materiality to the process creates considerable cost-prohibitions (as well as increases in embodied carbon) when considered at commercial scale. Supply chain issues related to the increased need for substrate material and exogenous, structural inputs alone would negate the widespread commercial viability of prior art's process with respect to creating structural building materials. The present invention provides a state of the art that eliminates those impediments to scalability for creating rigid, structurally capable mycelium biocomposite parts. The present invention's simplification of multiple aspects of the prior art, reduces costs and complexity in manufacture. This reduction in cost and complexity has an exponential effect on the wide range of commercial applications of the present invention.

Prior art rely on energy intensive and cost prohibitive pre and post processing to attain modest improvements in compressive strength. But the greatest improvements to physical characteristics (e.g.-surface hardness, density, etc.) or mechanical capabilities (e.g.-compressive strength, elasticity, tensility, etc.) can be achieved through simple improvements in fungal ecology. These improvements are related (but not limited) to the nature of the mold (fabric forms without rigid enclosures, e.g.) and the three-dimensional geometry that the inoculated substrate is grown in (hollow sections, e.g.).

The ability to enhance mycelial growth, specifically the rate of growth and the variety and quality of hyphae and their bonds, through fabric forming is a function of the tropism inherent in mycelium that responds to physical barriers and chemical cues alike. The fabric form provides three important signals for the mycelial growth process: pressure, access to nutrition, and the ability to respire. The pressure provided by the stockinette of the exterior fascia of the present invention holds the substrate together tightly enough to positively influence the quality and density of hyphal growth. The stockinette fiber choice can influence the growth of the organism by way of its lignin and cellulose content as a nutritive source for the mycelium. As a highly organized, yet limited resource, the weave of the external fascia signals to the fungal organism that there is a clear pathway for growth that is unobstructed. This organization of hyphae along the highly organized fibers of the stockinette's weave serves as a nano-structural scaffolding for hyphal growth. Due to the characteristics of hyphal extension along a structure like the warp and weft of stockinette, the present invention benefits from a very rigid, final structure as well as very hard, bone-like exterior faces that are the result of self-replicating mycelium without the aid of exogenous structural inputs that impart their own mechanical strength.

Prior art describe bone-like surface qualities, but the prior art would suffer from inconsistent expression of the bone-like hyphal expression without the benefit of the present invention's external fascia providing a scaffolding for uniform growth. Finally, the present invention benefits from a greater ability to tune consistent surface performance due to the ability for the external fascia to help the organism self-regulate respiration and moisture. An additional ability to easily introduce moisture as needed for optimal growth is enhanced by the fabric formed process of the present invention. Spraying the part with $H_2O_2$ during fermentation helps to stave off the potential for surface infections; but more importantly, because $H_2O_2$ quickly breaks down into $H_2O$ and $O_2$, the organism is supplied with critical water and oxygen. Moisture monitoring and correction are both greatly enhanced for the practitioner using the present invention. Prior art have relied on rigid molds or a series of rigid molds to create the final part's geometry that result in an inability to closely monitor and easily correct moisture issues during fermentation. The improvements to the state of the art by the present invention results in a more predictable and tunable result for rigid, structural applications for a new class of mycelium-based biocomposites.

Prior art depicts processes that produce materials that are suited for non-structural, non-rigid applications. The commercial success of these materials are recognized as 1:1 replacements for:
  Petroleum based foam packaging products
  Animal/synthetic leather textiles
  Foam/plastic based acoustic panels Though prior art describe aspirations of mycelium composites that can serve structural roles, the previously mentioned shortcomings of the methods described in the prior art are well documented in the academic literature regarding mycelium based materials. Many researchers have deduced that the previous state of the art was unable to produce even the smallest scale bench prototype that could be considered structural in nature. The foam-like qualities that are resultant from the processes described in prior art have heretofore driven interest in mycelium-based biocomposites away from structural applications and toward applications that require a less robust mechanical profile and/or toward applications that serve to supplant animal products in the textile and food sectors. Certainly, to date, there have been no commercially viable mycelium biocomposite processes described in the literature, or in prior art, that can be considered a 1:1 replacement for timber building products and other incumbent structural building materials that currently rely on petrochemicals or harmful extraction practices. Nonetheless, there have been several publications that express a desire to move toward a future where mycelium-based biocomposites can create viable building materials that can reduce the global reliance on timber products.

Rigidity in mycelium-based biocomposites is chiefly a function of density. Prior art cannot create parts (except through heavy compression) with adequate density to carry structural loads due to the incomplete fermentation that is a result of relying on rigid molds. Prior art describe processes that would rob the organism of much needed respiratory gases required to colonize densely packed substrate particles. The present invention can create rigid parts with a more compact, smaller dimensioned, discreet particle size than was previously possible. The benefits of the present invention are especially relevant when creating parts that are of the size and scale necessary to create structural building materials. Prior art can only benefit from higher densities as a result of applying industrial pressures post-fermentation.

An important aspect of the present invention is the introduction of a hollow core to any part that is made with the process described herein. The hollow core serves to create a manifold exterior surface that has a significant reduction in mass of substrate needed to create a part of the same volume; much in the same way that hollow structural section (HSS) is engineered. The hollow sections of this preferred embodiment of the present invention allow for an even greater enhancement to mycelium's ability to locate and consume nutrients and to properly respirate while doing so due to the reduced volume of substrate available to the organism. This impacts the timeframe needed to create strong parts since there is a shortened time within which the mycelium can fully colonize the substrate. This reduction in timeframe for growth also creates dramatic reductions in the risk of competing infection that can potentially ruin a production run. The benefits of the hollow section reduces costs through improvements in efficiency of manufacture due to: reduction in infection rates, significant strength-to-weight gains, reduction in complexity of manufacture.

Further reductions in the embodied carbon of the manufacturing process over prior art using the present invention are seen through the elimination of: heat pressing, substantial mechanical compression, exogenous rigid structures, infusion of resins/adhesives, cost prohibitive strength-to-weight ratios that utilize greater quantities of material.

These qualities make the present invention a suitable option for creating appropriately rigid structures with mycelium as the composite's matrix and agricultural waste as the composite's reinforcement to serve in structural/load-bearing applications without the need for exogenous, structural inputs. This fills a long sought after need in the marketplace for a plant and fungus based alternative to timber products.

Furthermore, finding ways to utilize agricultural waste streams for building materials is a very impactful method for regeneratively producing building materials that have a net negative carbon footprint. A major component of that impact is found through the exponential impact of creating 1:1 replacements for timber products. Reducing demand for forest timber reduces harvesting pressures on the earth's forests in general. This reduction in pressure results in a better ability for our remaining forests to sequester $CO_2$ and produce life giving $O_2$. Each 2×4 that is left standing as a part of tree in a forest has an enormous benefit to the fight against climate change.

The marketplace for timber products have begun to exhibit the deleterious effects that Peak Oil has had on the cost to extract petrochemicals (market price volatility, resource scarcity, increases in extraction costs). It has been long understood that the rate of extraction of timber from our forests is outstripping the ability of those forests to recover, and so even though timber is ostensibly a renewable resource; we have reached a rate of consumption that has produced a Peak Timber scenario.

These types of 'peak' scenarios have the positive effect of galvanizing public recognition of the true ecological costs of timber extraction. These 'peak' scenarios also expose the waning value proposition for timber products in general. The market volatility in the timber market will not abate if the status quo is left in place. A significant reduction in timber product consumption can also help to regenerate our forests faster.

The first objective of the present invention is to describe a process that results in an industrial grade building material that can serve in a variety of structural, load-bearing applications and/or rigid applications. A second objective of the present invention is to provide a simplified method for creating stronger parts with greater variability in the final part's geometry and dimensions. A third objective of the present invention is to provide a method of fabric forming that greatly contributes to the ability to create stronger parts through an enhanced ability to monitor and control the fungal ecology throughout the process. This enhancement allows the practitioner of the process to tune the final physical characteristics and mechanical capabilities. A fourth and final objective of the present invention is to provide a method to create a structural, load-bearing mycelium based biocomposite that can produce parts that can be regeneratively produced at commercial scale. These and other advantages will be more clear with the following description of the components and methods of the present invention.

When discussing the present invention, the following definitions will be helpful (italicized words denote cross-referenced terms):

admix—refers to a mixture of nutritive and non-nutritive particles added to the inoculated substrate. This mixture provides nutrients that: enhance mycelium growth, improve the substrate's discreet particle compaction through particle reinforcement within the inoculated substrate, and introduces plasticity to the inoculated substrate.

composite material—a material that is derived from two or more constituents with markedly dissimilar properties (chemical and physical). At least one of the constituents is a matrix and at least one is a reinforcement. The constituents combine without dissolving to form a new material that has new, superior properties than the individual constituents.

covering—referring to the external fascia of the finished part disruptive disturbance—refers to the introduction of a sudden change to the fungal ecology of a fungal organism's substrate where a previous set of conditions is replaced (completely or partially) by another set of conditions pertaining to at least one nutrient and one environmental variable. Examples of this type of disruption would be agitation, compaction, vibration, etc. of the substrate.

enrichment disturbance—refers to the introduction of a sudden change rate and amount of nutrient supply to the fungal organism during fermentation.

external fascia—this refers to the stockinette or other textile that is used to cover the inoculated substrate during fermentation. The fascia has a specific fiber type, weave, warp, and weft that facilitates uniform mycelium growth across the entire surface of the finished part. The external fascia should provide a low level of compression (3-15 mmHg) for the inoculated substrate. The pattern created by the weave of the fascia also acts as a scaffolding along which the mycelium will grow, forming a highly organized nano-scale bracing across the entire surface; increasing the surface hardness and decreasing likelihood of wall rupture under load.

fabric form—a flexible, consumable tool that is used to contain the inoculated substrate during fermentation. After fermentation, the fabric form is integrated into the finished part as the external fascia.

fermentation—in the context of the present invention, fermentation is the metabolic breakdown of an organic substrate by the enzymes secreted by the mycelium of a filamentous fungi.

fungal ecology—refers to the specific study of fungal behavior in relation to a given set of environmental variables. Different, quantifiable aspects of mycelial growth and distribution, quality and turgor can be described in relation to the fungal ecology of a given organism. The distribution, presence or absence, and descriptive nature of these quantifiable aspects are important to the accurate application of the most economical use of environmental variables possible for a given structural need. The variability of responses (known collectively as K-selection and r-selection strategies) to stresses or disturbances to substrata that a particular fungal species may have given a particular set of environmental variables is of particular interest to the present invention. Two types of controlled disturbances are introduced during the process of manufacture of the present invention, disruptive disturbances and enrichment disturbances, to bring about predictable, beneficial behavior of mycelium during fermentation.

hollow cylinder—refers to the three-dimensional geometry of the preferred embodiment of the present invention that can most accurately be described as a right circular hollow cylinder.

hollow structural section (HSS)—a type of hollow metal tubing used in structural applications. The profile of HSS can be square, circular, rectangular, or elliptical. The square and circular profiles are especially efficient structural framing members due to their uniformity along multiple cross-sectional axes.

industrial compression—refers to a manufacturing process that makes use of an industrial press to supply large, downward forces to a work piece.

inoculated substrate—refers to a mixture consisting of: the fungal organism whose mycelium self-replicate to form the composite matrix, the substrate which provides the composite reinforcement, and the admix which provides the mycelium with nutrition and also provides particle reinforcement to the composite internal textile—refers to a textile used in the preferred embodiment that is used to entrap the discreet particles of the inoculated substrate during manufacture. The internal textile also serves as a continuous fiber reinforcement to enhance the weak phase of the mycelium matrix.

inverted mold—refers to a tool that is used to wind the assembly that includes the internal textile and the inoculated substrate in the direction of the long axis of the part to create the profile of the finished part. During fermentation, the inverted mold provides a physical barrier that interfaces with the interior aspect of the manifold surface of the hollow cylinder or any other profile created with the present invention. The physical barrier promotes outward mycelial growth, thereby improving the uniformity of the fermentation process.

K-selection—refers to the strategies of fungal mycelium whereby they reach optimal population size in relation to their environment.

manifold surface—refers to the continuity of the surface of the finished part that is created by the external fascia. The preferred embodiments of the present invention are preferentially formed into developable, manifold surfaces that are typical of Riemannian manifolds. The efficiency of this type of geometry is useful for the intended use of the present invention as a structural building material.

matrix—the binding constituent of a composite material. In the context of the present invention, the matrix is provided by the self-replication of mycelium.

mycelium-based biocomposite material—a composite material that employs mycelium as the matrix and uses unadulterated, natural fibers as reinforcement.

profile rail—refers to a profile used to create a template for the inoculated substrate. In the preferred embodiment of the present invention, the profile rail provides a uniform surface upon which a roller can tamp down the inoculated substrate to the proper density. The design of the profile rail is such that, when the final revolution of the rotational operation is complete, the desired sectional profile is achieved.

r-selection—refers to the strategies of fungal mycelium related to their intrinsic rate of increase in population size in response to a specific set of fungal ecological parameters.

reinforcement—the structural, strong phase of a composite material. In the context of the present invention, the reinforcement is chiefly provided by the substrate. Additional reinforcement is achieved through inclusion of an admix and the employment of an internal textile.

stockinette—a tubular length of textile. Typically cylindrical in profile, its flexibility in all directions allows for the easy creation of faces and edges when employed as the mold and subsequent external fascia for the present invention. Computer aided design can achieve stockinette constructions that can facilitate improvements in mechanical performance. The warp and weft as well as the weave and profile of the stockinette can be finely tuned to enhance the nanostructural scaffolding provided to the mycelium during fermentation.

substrate—refers to the organic and inorganic materials used as a main nutritive vehicle for the mycelium. The nutritional content of the substrate can be tuned for desired end product performance. Specifically, the lignin, cellulose, and hemicellulose content of the substrate should be considered. Discreet particle size and shape of the substrate should be considered with respect to surface resolution and density of the final part. The substrate is ideally a homo- or heterogenous mix of regionally supplied agricultural waste products that have no human food value. The substrate provides the main reinforcement constituent of the mycelium-based biocomposite material.

warp and weft—refer to the longitudinal and transverse (respectively) orientations of fiber yarns of a weave such as that in a stockinette or in the internal textile. The three-dimensional construction of the warp and weft of the stockinette or internal textile can provide organized scaffolding designed to tune the performance of the final part's surface characteristics and overall durability and strength.

Components of Composite

Referring to FIG. 1A, together, the following constituents of the composite material derived from the present invention form what is known in the present invention as inoculated substrate 199:

Matrix

Pre-select a suitable species of fungus that is well adapted to the pre-selected program of fungal ecological parameters throughout the fermentation stage of manufacture. The pre-selected species should be chosen for the quality and variety of hyphal morphologies most suitable to the desired performance characteristics of finished part 300.

Inoculate a suitable ratio of fungal mycelium to starter substrate to begin the organism's colonization.

Prepare inoculant for introduction into substrate.

Reinforement

Preselect a substrate with a suitable discreet particle size for the desired final density. A smaller, more uniform discreet particle size will yield a more dense part. A more dense part will yield a stronger part. There is an upper and lower limit to optimal discreet particle size and density for a particular substrate. Ideally, a substrate is pre-selected that is regionally available as agricultural waste, and will perform the proper nutritional role for the pre-selected fungal species and pre-selected program of fungal ecological parameters throughout the fermentation stage of manufacture. Another consideration for pre-selection of substrata is that it will end up forming the final supportive structure for finished part 300. Intrinsic qualities of the pre-selected substrate (surface hardness, etc.) will have an effect on the performance of finished part 300 post-fermentation.

Determine appropriate moisture content for the substrate. This optimal moisture level will ensure that the ratio between moisture and respiratory efficiency for the fungal mycelium is ideal for rapid growth.

Additional admix constituents can be considered. These additional nutritive and non-nutritive constituents can be tuned to effect both trophic and tropic behavior of the fungal mycelium. These admix constituents can also provide plasticity to the inoculated substrate mix which can aid in forming the final geometry with low pressure templates and jigs (refer FIG. 4A). The added plasticity can have other beneficial effects on the process of manufacture. Another benefit of the admix constituents can be in providing a reduction in pore size of the substrate. Filling in the pores of the compacted substrate with a nutritive constituent of different nutritional value can provide a robust increase in the overall adhesion of the matrix to the discreet reinforcement particles and the internal textile, resulting in a stronger part than otherwise achievable without the admix.

Additional Reinforcement

Pre-select a textile suitable for use as internal textile 200. Internal textile 200 serves to trap the discreet particles of the inoculated substrate together during manufacture. After formation, internal textile 200 provides a means of compartmentalizing the mass of substrate. This creates channels where the fungal organism can delineate clear gradients in overall food source. This enhances mycelial growth by engaging a part of the fungal organism's K-selection strategy. Of note regarding the selection of a suitable textile for use as internal textile 200 is consideration of the weave and the warp and weft of the textile. These 3-dimensional structures that are part of the internal textile's physical makeup can be engineered to promote desired mechanical characteristics in the final part. As part of the fungal mycelium's r-selection strategy, the fungal mycelium will build strong bonds with internal textile 200 ensuring that the food source contained therein (namely, the substrate and admix) is preferentially sequestered for the sole use of the fungal mycelium itself. By providing an engineered structure to the weave of internal textile 200, the rapid growth of the mycelium through the pores of the textile will be enhanced in the final part. The fiber content of internal textile 200 yarn is another important consideration. Providing a fiber with a desirable nutritional profile can help to promote a tunable heterogeneity throughout the entirety of finished part 300. For instance, by providing a yarn with a slightly higher nitrogen content than the main substrate and the admix, internal textile 200 will provide a tunable region within finished part 300 where there will be enhanced mycelium growth. These tunable regions provide a considerable improvement in compressive strength for finished part 300 without any additive industrial inputs or post-processing. Dramatic improvements over prior art in embodied carbon of a finished part 300 created with the present invention. The gains enjoyed by the present invention in embodied carbon are had with a low-tech solution that yields a stronger part than prior art.

The admix can also contain pre-selected components such as tree nut shells and husks, or any other similar agricultural waste composed of naturally hard materials. The hardness of the pre-selected material and its discreet particle size and uniformity will determine the degree to which such an admix component will improve compressive strength and/or surface hardness of finished part 300.

External Fascia

Some care should be taken when considering the structural nature of the textile used to weave stockinette 210, which creates the inoculated substrate's cover during formation, and subsequently serves as an integrated external fascia to finished part 300. As with the three-dimensional structures of the warp and weft, the overall weave configuration can have an impact on the strength of the final part. This improvement in strength results from a nano-structural scaffolding provided by the criss-crossing fibers of the stockinette's weave. The K-selection strategies of the fungal mycelium will maximize growth along the pathways provided by stockinette 210. This hyper organization across the entire exterior surface of finished part 300 dramatically improves several aspects of the finished part's physical characteristics. Surface hardness, abrasion and impact resistance, as well as a measurable increase in the resistance to deformation of substrate particles oriented to form the sub-surface of the part all contribute to part service life and inhibits buckling during axial loading. The pore size of stockinette 210 will have an impact on the ability of the covering to create a desirable moisture gradient for inoculated substrate 190. The pore size of stockinette 210 also allows for optimal respiration of the organism. The rate and quality of growth for fungal mycelium is directly impacted by the organism's access to water as well as access to adequate pressure gradients which allow sufficient gas exchange for complete cell respiration during fermentation of the inoculated substrate and its sub-components. This breathable outer layer with moisture holding capacity provides an ideal environment for creating very rigid finished parts with desirable mechanical capabilities that allow for structural applications.

The external fascia in the preferred embodiment provides the surfaces for the right circular hollow cylinder of finished part 300. Four distinct surfaces regions are formed in the finished part 300. A top annular surface 330 and bottom annular surface 331 bound to an inner surface 320 (a right circular cylinder) and an outer surface 340 (a right circular cylinder). Inner surface 320 and outer surface 340 form concentric right cylinders in the preferred embodiment.

Tools, Molds, and Templates

Referring to FIGS. 1A-1E & 3A-3C, together, the following items compose the basic tools and templates necessary to create a part of the present invention:

Inverted Mold Tool

An important aspect of the present invention is the ability to ferment the part in an open environment. This allows for more robust gas exchange within the mycelium during fermentation. In the present invention, gas exchange gradients are regulated within the fermenting part by the fungal organism. This is achieved through inverting the orientation of the rigid growth molds that prior art describe. Prior art rely on adding an inoculated substrate mixture to a rigid enclosure with small air holes for gas exchange. This results in a build-up of $CO_2$ within the part during fermentation. Built up $CO_2$ can have an inhibitory effect on the fungal mycelium's rate of growth. Completely eliminating a rigid form, mold, or enclosure for the mycelium to grow against is not advantageous. In the present invention, a fabric form replaces the rigid outer structure of prior art. This fabric form is enhanced through the addition of a rigid form through the interior aspect of the part called an inverted mold tool 220 that forms an inner void 310 in finished part 300. By providing a rigid center form to grow against, a thick, uniform mass of anastomosed hyphae grow along a section of the fermenting part that will form interior face 320 that extends between top 330 and bottom 331 annular rings of the preferred embodiment of the present invention. This increases the overall stiffness of finished part 300, which increases compressive strength when under various loading scenarios.

Internal mold tool 220 has the added benefit of creating a unique geometry within finished part 300 that serves to dramatically improve its strength to weight profile. In the preferred embodiment, finished part 300 is fashioned into a right circular hollow cylinder with inverted mold tool 220 forming an inner void 310. Consideration should be made when choosing the dimensions of inverted mold tool 220 as there is a direct impact on the volume of the wall of the hollow cylinder in correlation to the outer diameter of finished part 300. The diameter of inverted mold tool 220 will determine the degree of strength-to-weight gains or losses in a final part's design.

In the preferred embodiment, a simplified method of manufacture uses inverted mold tool 220 to wind internal textile 200 into an overlapping spiral structure (when viewed in profile along the long axis of the centroid of inverted mold tool 220) that incorporates a single layer of stockinette 310 as innermost layer 320 with inner textile 200 as the second layer, entrapping the first layer of inoculated substrate 190 as inverted mold tool 220 continues to rotate along an axis that is perpendicular to profile rail 240. The pre-determined profile of inoculated substrate is rolled in subsequent revolutions of the tool in a manner to form a suitable final profile of the part.

During fermentation, inverted mold tool 220 can be used to hang a succession of parts in a tight group to save space in a fermentation chamber. Using a longer inverted mold tool 220 than finished part 300 will facilitate in moving the part from station to station during manufacture.

At the end of fermentation, inverted mold tool 220 is removed from finished part 300 before drying.

In the preferred embodiment, finished part 300 is a right circular hollow cylinder. To create a strong internal inner void 310 that is square to the hollow cylinder's external surface, inverted mold tool 220 has a profile that matches the profile of finished part 300. It is conceivable that there is a design preference (either for strength, aesthetics, or a combination of the two) that either the outer profile of the finished part or that of the inner void 310 have a different geometric profile than a simple ellipse. In conjunction with a design change to profile rail 240, inverted mold tool 220 can be composed of a different geometric profile capable of producing a myriad of other outer and inner profiles advantageous to the final design of a finished part (Refer to FIGS. 12B-12E).

Profile Rail Template

The present invention comprises a finished product 300 that is a right circular hollow cylinder in the preferred embodiment. This shape is advantageous as a building material and has obvious structural advantages. This shape is also conducive to a simplified process of manufacture. The preferred embodiment describes a method whereby a person having obvious skill in the art could produce a part of considerable strength and structural capabilities with very simple tooling and using only hand powered tools to form the part.

In order to provide a consistent, quality building material, the profile of the material should be consistent and uniform in makeup throughout the length of the part. The rolling method of the present invention can be tuned to produce a uniform profile of nearly limitless geometries. The simplest version is to determine a profile curve that results in a right circular hollow cylinder.

Considerations when determining the slope and pitch of the curve include the composition of inoculated substrate 190 and the physical characteristics of internal textile 200 and external fascia 210.

When designing the profile, the even compaction of the discreet particles of inoculated substrate 190 should result in a predictable final profile with the desired final geometry and dimensions.

In the preferred embodiment of the present invention, profile rail 240 is used as a template to create a mass of inoculated substrate 190 in a profile that will result in a right circular hollow cylinder with a particular set of pre-determined dimensional attributes. The benefit of a CAD program and a CNC machine can aid in the creation of precise rail profiles that can be utilized for tens of thousands of production cycles when conceived at commercial scale. The further use of CAD and robotic manufacturing can produce any number of conceivable profile geometries tuned to the desired physical characteristics and mechanical capabilities of a finished part.

It can alternatively be conceived that a machine can be created that can robotically spread and compact the inoculated substrate in a desired profile at a very precise density throughout the profile. Profile rail 240 in this alternate embodiment is of digital origin.

In another alternative embodiment, a simple mass of inoculated substrate can be spread and compacted in any manner, without the aid of profile rail 240 so as to create an irregular profile shape in a finished part.

In the preferred embodiment of the present invention, two parallel profile rails are fixed at a pre-determined distance apart on a board to create rolling template 230.

The preferred embodiment of the present invention describes a simplified, manual technique to create a structural part. The aspects of the present invention are all meant to be alternately and preferentially conceived of at a commercial scale. Various auto-tensioning rollers and other automated industrial tooling may be employed when designing large-scale processes to perform the same basic manual functions described in the preferred embodiment.

Process Flow Chart (FIGS. 2A-2F)

The preferred embodiment's method of manual manufacture is described in FIGS. 2A-2F (excluding optional steps 905.2 & 906). The detail of the text provided in FIGS. 2A-2F allows for the text depicting the process to speak for itself.

EXAMPLE #1

Detailed Description of Method to Manually Manufacture the Preferred Embodiment

General note—aseptic technique should be considered throughout. Steps to mitigate the embodied carbon of the PPE used for personnel and the process as a whole should always be considered; reusable equipment should be standard. Using effective steam surface cleaning along with regular cleaning of all surfaces that come in contact or near the field of manufacture is desirable. This aseptic upkeep is especially necessary for the first several hours of fermentation (species and ecology specific), typically in the range of 24-36 hours. Aseptic technique should be considered for personnel throughout the process. As the timing of the process approaches the initial drying sequence (FIG. 2F, step 907), the organism has become well established and the likelihood of infection is quite low, however aseptic vigilance is still maintained throughout all of the room's surfaces. The parts that are going to be dried can be aseptically handled to quickly perform some quality measurements and tests, if necessary. Handling of parts should be minimized until after the last drying sequence cycle has completed and the part has reached room temperature. After that point (several days into the process), no aseptic technique is required as the fungal organism is inactive and the part has been thermoset during the previous drying phase, such that it has obtained it's final geometric form.

1. A part was created using the process outlined in FIGS. 2A-2F. The following dimensions and characteristics were observed and recorded. A series of test specimens were created and tested. Average test observations and recordings were comparable to the following sample.
   1.1. height—200 mm
   1.2. inner diameter—49 mm
   1.3. outer diameter—100 mm
   1.4. mass of constituents
      1.4.1. start mass—inoculated substrate 190—625 g
      1.4.2. internal textile 200—15 g
      1.4.3. stockinette 210—19 g
      1.4.4. total start mass—659 g
      1.4.5. final dry mass of finished part 300—280 g (45% of total start mass)
   1.5. final dry density—0.25 g/cm$^3$
   1.6. final dry volume—1,136 cm$^3$
   1.7. overall shape—right circular hollow cylinder
   1.8. Compressive strength—0.98 MPa
   1.9. Young's MOE—53.11 MPa
2. Though the preferred embodiment created a part with a specific mechanical profile. Significant tuning of the inoculated substrate components can yield parts with different mechanical profiles. Certainly, with a greater density profile, a specimen created in the same manner as above would yield better mechanical capabilities. Further enhancements to the design and manufacture of the present invention can be achieved through the various alternate embodiments described below. Though extensive, the list is not exhaustive. The present invention describes a method for creating material that is useful in plethora of manufacturing sectors. The basic concepts described in the present invention can be modified to accommodate the needs of virtually all manufacturing sectors.
3. The process described in the preferred embodiment is also a rudimentary method for creating a base for tuning inoculated substrate 190 and/or admix formulations and for iterating a design for the weaves and structures of internal textile 200 and stockinette 210.

EXAMPLE #2

Low-Tech Means of Introducing New Geometric Form to a Pre-Formed Part

General note—low-tech here means that the process described requires very little embodied carbon, and can be largely employed manually. The purpose of designing the preferred embodiments as low-tech examples is to shop the simplified mechanisms that need to be scaled for commercial production.

Figures 4A, 4B:
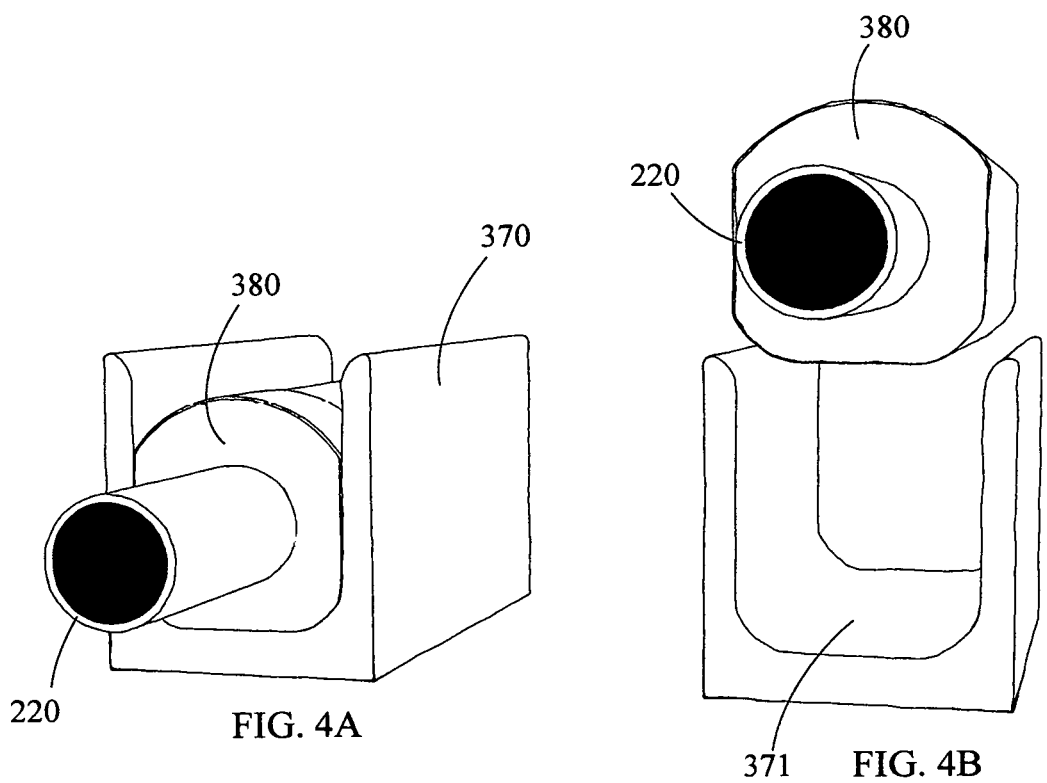

1. Referring to FIGS. 4A-4B, example #2 describes the process highlighted in FIG. 2E, step 905.2. In the early stages of the fermentation process (FIG. 2E, step 905.1), the part maintains some of the initial plasticity provided by the inoculated substrate's admix. A simple tool 370 designed to press a change or permanent deformation in the formed part's surface to create faces or features on the exterior surface using a unique tool geometry 371, creates an alternate finished part 380.
2. The disruption to the grown mycelium during deformation can stimulate growth within the disrupted ares of the inoculated substrate. It is believed that these stimulated growth areas will be rich with heterogenous hyphal morphologies beneficial to increasing the binding strength of the hyphal matrix.

EXAMPLE #3

Means of Incorporating a Pre-Formed, Engineered Structure to Enhance Mechanical Capabilities, or Provide a Means to all the Interface of Other Parts with the Newly Formed and Augmented Part 390

General note—The structure described in FIGS. 5A-5C is envisioned as an augmented structure 391 composed of a regeneratively sourced biological material that can remain integral to the newly formed and augmented part 390 due to its nutritive qualities provided to the growing fungal mycelium. Such an augmented structure 391 could replace the function of inverted mold tool 220 as a consumable, yet additional reinforcement to the newly formed and augmented part 390.

1. The design of the augmented structure 391 should reflect the mechanical needs of the intended use for the newly formed and augmented part 390.
2. The composition of the structure should be considered. A material choice that allows the overall mycelium-based biocomposite material to remain backyard compostable is desirable.
3. The method of manufacture for the augmented structure 391 will necessarily vary based on the material(s) chosen.
4. 3D printed structures made from filaments composed of all plant based constituents are an ideal choice, but the ultimate method for manufacturing the augmented structure 391 will be material dependent.
5. The design of the augmented structure 391 can include smaller sub-structures embedded within that impart enhanced ability for the newly formed augmented part 390 to interface with other items in a larger construction or superstructure.

EXAMPLE #4

The Basic Structure of a Right Circular Hollow Cylinder Made with the Present Invention General note—Referring to FIGS. 6A-6B

The design of the basic structure 300 made chiefly from mature mycelium growth 310 from the inoculate substrate 190 in accordance with the preferred embodiment also including an inner void 310.

EXAMPLE #5

Figure 7A:
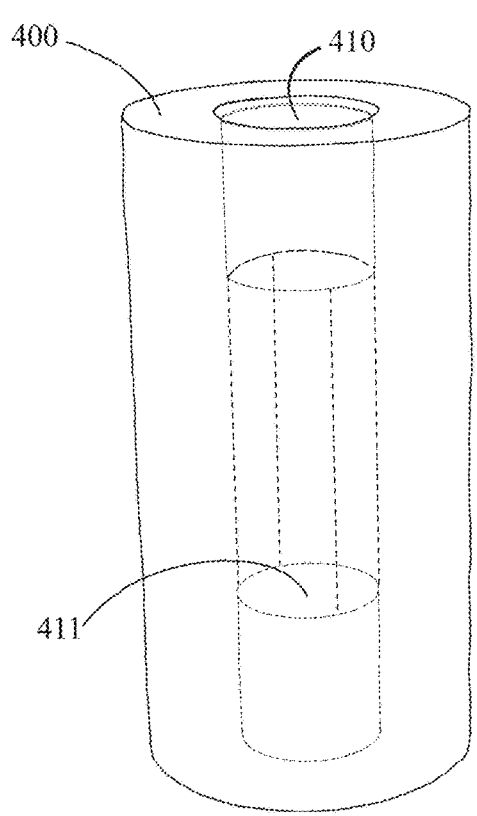
Figure 7B:
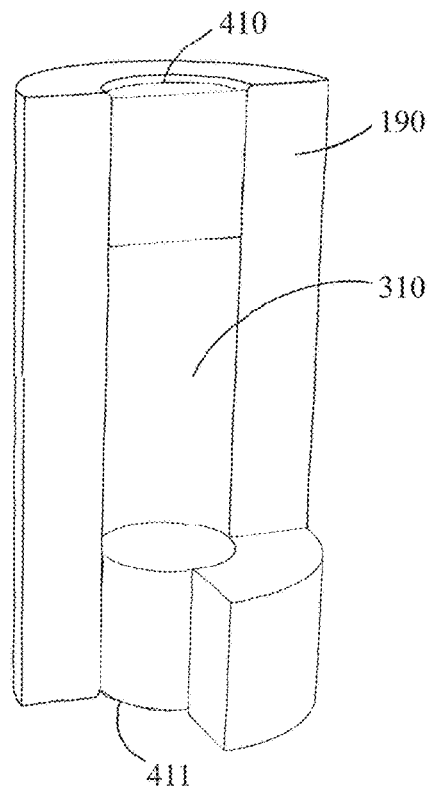

The Basic Structure of a Right Circular Hollow Cylinder with Multiple Plugs and A Remaining Inner Void 310 Made with the Present Invention General note—Referring to FIGS. 7A-7B The design of a basic structure 400 which includes top plug 410 and bottom plug 411 while still maintaining a reduced inner void 310. These plugs can help to increase compressive strength by adding an optimal mass of added material to a place that can aid in amount of force required to cause buckling. The top plug 410 and bottom plug 411 can be made of similar or dissimilar materials. The plugs will preferentially be made from a mycelium composite process similar to the process described here so that they can be adhered to the finished part 400 with mycelium as opposed to using an exogenous adhesive. If not from a mycelium-based biocomposite, the plugs can also, preferentially, be made from a biological based material that is backyard compostable while providing the necessary mechanical profile desired. The dead airspace inside the structure is advantageous for sound and thermal mitigation purposes.

EXAMPLE #6

Figure 8A:
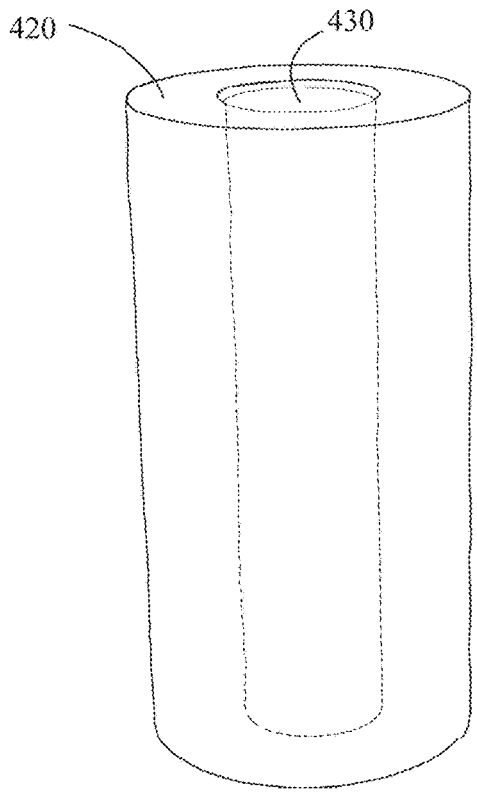
FIGS. 8A-8B—Filled cylinder
Figure 8B:
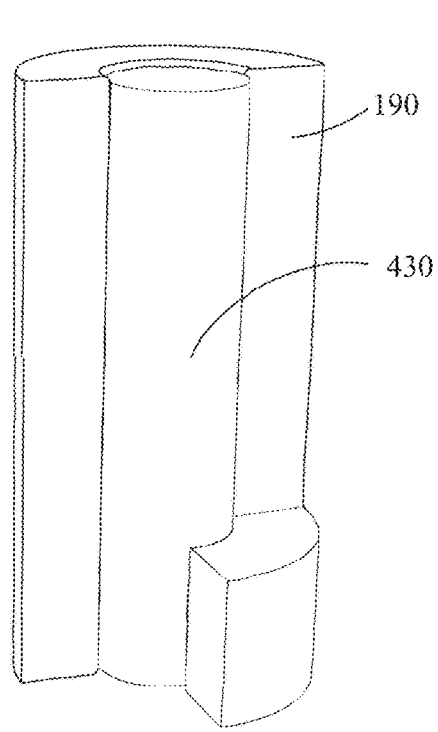

The Basic Structure of a Right Circular Hollow Cylinder Entirely Filled with an Inner Plug 430 Thereby Filling the Inner Void 310 Made with the Present Invention General note—Referring to FIGS. 8A-8B The design of the basic structure 420 with inner plug 430 and no remaining inner void 310. By filling the inner void with a full mass of material similar to the composition described above for top plug 410 and bottom plug 411, the overall strength can be greatly increased. Similarly to above inner plug 430 can be made of similar or dissimilar materials to finished part 420. The inner plug 430 will preferentially be made from a mycelium composite process similar to the process described here so that it can be adhered to finished part 420 with mycelium as opposed to using an exogenous adhesive. If not from a mycelium-based biocomposite, inner plug 430 can also, preferentially, be made from a biological based material that is backyard compostable while providing the necessary mechanical profile desired. The change in density inside the structure is particularly advantageous for sound and thermal mitigation purposes.

Figure 9A:
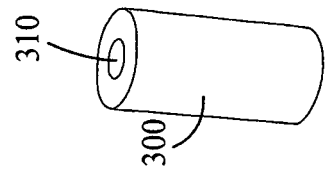
Figure 9B:
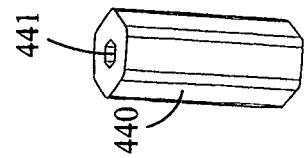
Figure 9C:
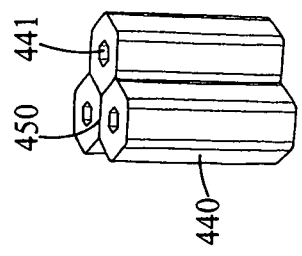

Referring to FIGS. 9A-9F, there are a multitude of profiles that the finished part can take when made with the present invention. FIG. 9B shows a hexagonal profile 440 with an annular hexagonal profile for the hexagonal inner void 441. The multitude of hexagonal finished parts 440 in FIG. 9C are joined together by mycelial bond 450 that employs the adhesive qualities inherent in mycelium to strongly bind disparate parts together to form larger super structures. These larger superstructures can be grown together to create larger load bearing structures than would otherwise be possible when grown in a monolithic way.

Figure 9D:
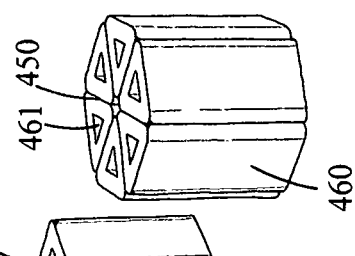

FIG. 9D shows another such superstructure made from a triangular profile 460 finished part with an annular triangular profile for the triangular inner void 461. The multitude of triangular finished parts 460 are joined together by mycelial bond 450 that employs the adhesive qualities inherent in mycelium to strongly bind disparate parts together to form larger super structures. These larger superstructures can be grown together to create larger load bearing structures than would otherwise be possible when grown in a monolithic way.

Figure 9E:
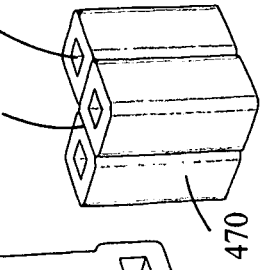

FIG. 9E shows another such superstructure that can be used in the corner interface of a building or similar type structure. The superstructure is made from square profile 470 finished parts with annular square profiles for the square inner void 471. The multitude of square profile finished parts 470 are joined together by mycelial bond 450 that employs the adhesive qualities inherent in mycelium to strongly bind disparate parts together to form larger super structures. These larger superstructures can be grown together to create larger load bearing structures than would otherwise be possible when grown in a monolithic way.

Figure 9F:
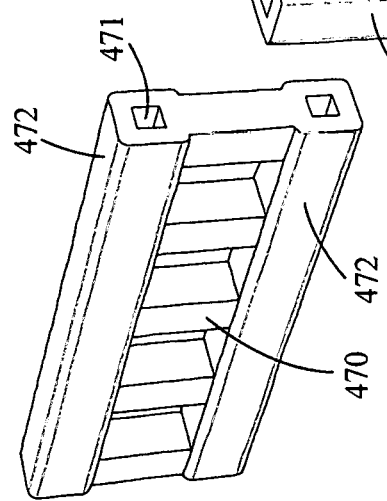

FIG. 9F shows a structure grown from two elongated square profile finished parts 472 and several smaller square profile finished part 470 that are joined together through mycelial bond 450. The larger superstructure has distinctly stronger mechanical capabilities of the individual parts and also stronger mechanical capabilities than a part grown in the same final geometry in a monolithic way.

The previously mentioned embodiments of the present invention are representative of prototypical forms achievable with the least amount of cost and effort to manufacture finished parts at commercial scale. The following alternative embodiments show a whole range of possible methods of employ to manufacture the present invention.

Special attention is made to envision scaled versions of the manual process described above. The rolling method of manufacture provides a means of scaling the length of a finished to a theoretical infinite amount without increasing fermentation time, the only limit being the size of tooling available. A 200 mm length of a 100 mm O.D., 50 mm I.D. hollow cylinder section would take the same length of time to grow as a 2000 mm hollow cylinder section with the same I.D. and O.D. The several advantages mentioned above promote the production of larger scale parts that would not suffer from the previously elucidated issues associated with growing a part of the same size and scale with methods described in prior art.

In an alternative embodiment of the present invention, roller template 230 can be of sufficient size to manufacture a part that is 200 mm O.D., 120 mm I.D.×3000 mm in length. The internal textile 200 can be supplied to the bed of the template from a roller. An overhead hopper can supply a controlled release of inoculated substrate 190 over the large bed area. A large roller can uniformly compact inoculated substrate 190 between the large spacing between profile rails 240. The size of inverted mold tool 220 necessary for such a large part would benefit from being on a large, mechanized spindle that can be ratcheted to create tension while rolling internal textile 200 and inoculated substrate 190, just as described in step 904.1 of FIG. 2D. A tensioning roller placed immediately in front of inverted mold tool 220 spindle (in the direction of spindle rotation) can tamp down inoculated substrate 190 that is immediately adjacent to the transition from template to part. This tamping would help to keep such a large area of inoculated substrate 190 uniformly dense during rolling process 904.1. A predetermined amount of tension can be applied to internal textile 200 by maintaining adequate distance between inverted mold tool 220 spindle and the roll at the opposite end of the bed that holds internal textile 200. This tension serves to create adequate compression of the discreet particles of inoculated substrate 190 during rolling process 904.1. The amount of tension, and thereby, the amount of compression applied to inoculated substrate 190 can be tuned to achieve certain mechanical capabilities in a finished part.

In another embodiment, the apparatus described in the previous paragraph can benefit from the use of a jig that can be placed over the newly formed part, covering the outward face of the assembly 350. This jig aids in applying the excess 280 stockinette 210 over the assembly, thereby becoming the external fascia of the outward fascia 340.

In another embodiment, after rolling step 904.1, the part can be enveloped in a cover manufactured using a pultrusion method. The precision of the weave can achieve desirable, tunable results in that can aid fungal ecology during fermentation as well as providing mechanical advantages to a finished product.

In another embodiment, the entire assembly including: inoculated substrate 190, internal textile 200, inverted mold tool 220, stockinette 210 can be assembled using a pultrusion method of manufacture. This method, employed earlier in the manufacturing process can aid in reduction of material waste while also benefitting from the ability to create finished parts of virtually limitless length. This reduction in material waste can further improve the embodied carbon profile of a finished part. This reduction in waste is also coincidentally gained with the ability to create a stronger part with more uniformly applied strength characteristics throughout a finished part's structured matrix. These efficiencies combine to improve overall quality and reliability when parts are produced at commercial scale.

In another embodiment, larger parts with O.D. in excess of 1000 mm and wall thicknesses of at least 50 mm and cylinder height of virtually unlimited length can be grown and cured. The cured, large cylinder shell (or whatever other shape is desirable) can serve as a biologically derived form for concrete, or some other formable building material. The form can stay integral to the structure, not unlike a Lally column, or be removed and composted.

In another embodiment, the entire assembly including: inoculated substrate 190, internal textile 200, inverted mold tool 220, stockinette 210 can be removed from the fermentation chamber (905.1) during the first 48 hours while the assembly is still plastic. Inverted mold tool 220 can be removed, and the remaining components of the assembly can be formed using any manner of forming, including manual, to sculpt or press a form of limitless possible ultimate geometries, including flat sheets, or curvilinear surfaces. Multiple assemblies can be joined together to create large superstructures that can be further fermented in a manner that allows the mycelium to permanently join the once disparate parts together in a larger, now integrally unified whole such depicted in FIG. 9F.

In another embodiment, one finished part 230 can become the inverted mold tool 220 for another part. Because of the makeup of the inverted mold tool 220 in this embodiment being another mycelium-based biocomposite can be integrated into the new finished part superstructure. A series of subsequent outer structures can be grown outside previous layers much like annular rings on a tree.

In another embodiment, air bladders can be employed as temporary inverted mold tools for very large parts that need to have large spans and maintain a uniform wall thickness. This method can created large shells that are self-supporting made entirely from the mycelium-based biocomposite of the present invention. The air bladders can then be deflated and easily re-used to form repeatable and/or unique structures.

In another embodiment, the joint structures can be created that can join multiple segments of finished part 230 to erect self-supporting structures.

In another embodiment, natural coatings can be applied to the surfaces of a finished part to enhance durability, especially in outdoor spaces or public spaces where the material may be exposed.

The present invention provides an improved method of utilizing agricultural waste and fungal mycelium in order to create mycelium-based biocomposite materials capable of serving in structural, load-bearing capacities. The dramatic reduction in the embodied carbon of a part grown with the method of the present invention over prior art creates benefit for the use of mycelium-based biocomposites in a new, regenerative economy. The present invention creates parts of superior strength over prior art using far less embodied carbon in the process of manufacture.

What is claimed is:

1. A method for creating a mycelium-based biocomposite material, the method comprising:
   determining an inoculated substrate and an internal textile for the mycelium-based biocomposite material;
   constructing the inoculated substrate with the internal textile;
   fermenting the constructed inoculated substrate to induce growth of the mycelium-based biocomposite material; and
   dehydrating the grown mycelium-based biocomposite material after fermenting the constructed inoculated substrate,
   wherein the grown mycelium-based biocomposite material being stiff, rigid, and load-bearing by having a density greater than 0.25 g/cm$^3$ (15.79 lbs/ft$^3$), a modulus of elasticity greater than 53 MPa (7,687 psi), and an ultimate compressive strength greater than 1.2 MPa (174 psi).

2. The method according to claim 1, wherein fermenting the constructed inoculated substrate to induce growth of the mycelium-based biocomposite material includes fermenting the constructed inoculated substrate to induce growth of the mycelium-based biocomposite material at a temperature between 22° C. to 26° C., and
   wherein dehydrating the grown mycelium-based biocomposite material includes:
   increasing temperature to 32° C. to 42° C.;
   drying the grown mycelium-based biocomposite material for at least 24 hours; and
   increasing temperature to greater than 75° C. after drying the grown mycelium-based biocomposite material.

3. The method according to claim 1, wherein determining the inoculated substrate and the internal textile for the mycelium-based biocomposite material further includes determining an external fascia for the mycelium-based biocomposite material, and
   wherein constructing the inoculated substrate with the internal textile includes constructing the inoculated substrate with the internal textile and external fascia.

4. The method according to claim 3, further comprising:
   determining a template and an inverted mold tool for shaping for the mycelium-based biocomposite material,
   wherein constructing the inoculated substrate with the internal textile includes constructing the inoculated substrate with the internal textile, the external fascia, the template, and the inverter mold tool.

5. The method according to claim 4, wherein constructing the inoculated substrate includes:
  laying out the internal textile onto the template;
  layering the inverted mold tool with the external fascia; and
  laying out the inoculated substrate onto the internal textile laid on the template.

6. The method according to claim 5, further comprising:
  spraying a predetermined liquid on the internal textile laid out on the template before laying out the inoculated substrate onto the internal textile laid on the template;
  spraying the predetermined liquid on the external fascia layered on the inverted mold tool after layering the inverted mold tool with the external fascia; and
  spraying the predetermined liquid on the inoculated substrate laid out on the internal textile laid on the template after laying out the inoculated substrate onto the internal textile laid on the template.

7. The method according to claim 5, wherein constructing the inoculated substrate further includes:
  rolling the internal textile onto the inverted mold tool layered with the external fascia; and
  covering the rolled internal textile with the external fascia.

8. The method according to claim 7, further comprising:
  spraying the rolled internal textile with the external fascia before covering the rolled internal textile with the external fascia.

9. The method according to claim 7, further comprising:
  selecting admix nutrients, wherein the admix nutrient are selected based on a predetermined density and hyphal phenotypical expression,
  wherein constructing the inoculated substrate further includes:
    adding the selected admix nutrients to the covered and rolled internal textile with the external fascia, the selected admix nutrients enhancing mycelium growth.

10. The method according to claim 9, further comprising:
  spraying the covered and rolled internal textile with the external fascia after adding the selected admix.

11. The method according to claim 3, wherein determining the inoculated substrate, the internal textile, and the external fascia for the mycelium-based biocomposite material includes:
  selecting a fungal organism;
  determining an inoculation method for the selected fungal organism;
  selecting an inoculated substrate type and particle size; and
  determining an inoculation method for the selected inoculated substrate type.

12. The method according to claim 1, wherein fermenting the constructed inoculated substrate includes:
  placing the constructed inoculated substrate in a fermentation chamber;
  setting a temperature of the fermentation chamber between 22° C. to 26° C.;
  setting an RH of the fermentation chamber to 85% to 100%;
  fermenting the constructed inoculated substrate in the fermentation chamber for at least 48 hours; and
  spraying the constructed inoculated substrate with a predetermined liquid at least every 12 hours.

13. The method according to claim 12, further comprising:
  disposing a growth pod around the constructed inoculated substrate during fermentation;
  spraying the constructed inoculated substrate with a predetermined liquid;
  increasing $CO_2$ concentrations;
  decreasing RH to 65% to 75%; and
  fermenting the constructed inoculated substrate with the growth pod placed around the constructed inoculated substrate in the fermentation chamber for at least 24 hours.

14. The method according to claim 13, further comprising:
  removing the growth pod from around the constructed inoculated substrate;
  spraying the constructed inoculated substrate with the predetermined liquid;
  increasing RH to 85% to 10%; and
  fermenting the constructed inoculated substrate with the growth pod removed in the fermentation chamber for at least 24 hours up to 14 days.

15. The method according to claim 14, further comprising:
  spraying the constructed inoculated substrate with the growth pod removed with the predetermined liquid at least every 12 hours.

16. The method according to claim 14, further comprising:
  dehydrating the grown mycelium-based biocomposite material, after fermenting the constructed inoculated substrate with the growth pod removed in the fermentation chamber for at least 24 hours up to 14 days.

17. The method according to claim 16, wherein dehydrating the grown mycelium-based biocomposite material includes:
  spraying the grown mycelium-based biocomposite material with the predetermined liquid, after fermenting the constructed inoculated substrate with the growth pod removed in the fermentation chamber for at least 24 hours up to 14 days;
  decreasing RH to below 40%;
  increasing temperature to 32° C. to 42° C.;
  drying the grown mycelium-based biocomposite material for at least 24 hours; and
  increasing temperature to greater than 75° C. after drying the grown mycelium-based biocomposite material.

18. The method according to claim 1, further comprising:
  placing the fermenting the constructed inoculated substrate in a predetermined shaped tool before disposing a growth pod around the constructed inoculated substrate during fermentation.

19. A method for creating a mycelium-based biocomposite material, the method comprising:
  determining an inoculated substrate, an internal textile, and an external fascia for the mycelium-based biocomposite material;
  determining a template and an inverted mold tool for shaping for the mycelium-based biocomposite material;
  laying out the internal textile onto the template;
  layering the inverted mold tool with the external fascia;
  laying out the inoculated substrate onto the internal textile laid on the template;
  constructing the inoculated substrate with the internal textile, the external fascia, the template, and an inverter mold tool by:
    rolling the internal textile onto the inverted mold tool layered with the external fascia; and
    covering the rolled internal textile with the external fascia;

fermenting the constructed inoculated substrate by:
  placing the constructed inoculated substrate in a fermentation chamber;
  setting a temperature of the fermentation chamber between 22° C. to 26° C.;
  setting an RH of the fermentation chamber to 85% to 100%; and
  fermenting the constructed inoculated substrate in the fermentation chamber for at least 48 hours;
after fermenting the constructed inoculated substrate in the fermentation chamber for at least 48 hours and during fermentation, disposing a growth pod around the constructed inoculated substrate, increasing $CO_2$ concentrations, decreasing RH to 65% to 75%, and fermenting the constructed inoculated substrate with the growth pod placed around the constructed inoculated substrate in the fermentation chamber for at least 24 hours;
after fermenting the constructed inoculated substrate with the growth pod placed around the constructed inoculated substrate in the fermentation chamber for at least 24 hours and during fermentation, removing the growth pod from around the constructed inoculated substrate, increasing RH to 85% to 10%, and fermenting the constructed inoculated substrate with the growth pod removed in the fermentation chamber for at least 24 hours up to 14 days; and dehydrating the grown mycelium-based biocomposite material, after fermenting the constructed inoculated substrate with the growth pod removed in the fermentation chamber for at least 24 hours up to 14 days, wherein the dehydrated mycelium-based biocomposite material being stiff, rigid, and load-bearing by having a density greater than 0.25 g/cm$^3$ (15.79 lbs/ft$^3$), a modulus of elasticity greater than 53 MPa (7,687 psi), and an ultimate compressive strength greater than 1.2 MPa (174 psi).

* * * * *